United States Patent
Federoff et al.

(10) Patent No.: US 10,162,940 B2
(45) Date of Patent: Dec. 25, 2018

(54) SYSTEM AND METHOD OF APPLYING STATE OF BEING TO HEALTH CARE DELIVERY

(71) Applicant: Georgetown University, Washington, DC (US)

(72) Inventors: Howard Federoff, Bethesda, MD (US); Ophir Frieder, Chevy Chase, MD (US); Eric Burger, Great Falls, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 15/058,949

(22) Filed: Mar. 2, 2016

(65) Prior Publication Data

US 2016/0180043 A1    Jun. 23, 2016

Related U.S. Application Data

(63) Continuation of application No. 13/549,890, filed on Jul. 16, 2012, now Pat. No. 9,305,140.

(51) Int. Cl.
*G06F 19/00* (2018.01)
*G06N 5/04* (2006.01)
*G06Q 50/00* (2012.01)
*G16H 10/60* (2018.01)
*G16H 50/20* (2018.01)

(52) U.S. Cl.
CPC ............. *G06F 19/345* (2013.01); *G06N 5/04* (2013.01); *G06Q 50/01* (2013.01); *G16H 10/60* (2018.01); *G16H 50/20* (2018.01); *G06F 19/3418* (2013.01)

(58) Field of Classification Search
CPC .... G06F 19/322; G06F 17/28; G06F 19/3443; G06F 19/3487; G06F 19/3481
See application file for complete search history.

(56) References Cited

U.S. PATENT DOCUMENTS

| | | |
|---|---|---|
| 6,789,091 B2 | 9/2004 | Gogolak |
| 6,904,428 B2 | 6/2005 | Frieder et al. |
| 7,720,869 B2 | 5/2010 | Frieder et al. |
| 7,886,000 B1 | 2/2011 | Polis et al. |
| 8,260,774 B1 | 9/2012 | Aggarwal |
| 8,380,531 B2 | 2/2013 | Paty et al. |
| 2001/0034639 A1 | 10/2001 | Jacoby et al. |

(Continued)

OTHER PUBLICATIONS

Aggarwal, "Social Network Data Analytics," Springer Science & Business Media, LLC, pp. 1-518 (2011).

(Continued)

*Primary Examiner* — Mariela Reyes
*Assistant Examiner* — Courtney Harmon
(74) *Attorney, Agent, or Firm* — Klarquist Sparkman, LLP

(57) ABSTRACT

A system for assisting a subject to select a proper form of treatment. The system comprises: a monitoring section that remotely monitors a health status of the subject; an inference section that infers medical information about the subject based on information subject posted on social networks; a subject database that stores subject's information; and a symptom engine that stores symptoms of medical situations. The inference section applies the health status and the medical information against symptoms stored in the symptom engine to determine a proper form of treatment.

24 Claims, 18 Drawing Sheets

(56) References Cited

U.S. PATENT DOCUMENTS

| | | |
|---|---|---|
| 2003/0033532 A1 | 2/2003 | Marks |
| 2005/0149869 A1 | 7/2005 | Kehr et al. |
| 2007/0061393 A1* | 3/2007 | Moore ............... G06F 17/3089 709/201 |
| 2008/0256444 A1 | 10/2008 | Wang et al. |
| 2009/0043714 A1 | 2/2009 | Zhao et al. |
| 2009/0048823 A1 | 2/2009 | Liu et al. |
| 2009/0083132 A1 | 3/2009 | Doganaksoy et al. |
| 2009/0172082 A1 | 7/2009 | Sufuentes |
| 2009/0319518 A1 | 12/2009 | Koudas et al. |
| 2009/0326981 A1* | 12/2009 | Karkanias ............. G06Q 10/10 705/3 |
| 2009/0327046 A1 | 12/2009 | Caller |
| 2011/0010366 A1* | 1/2011 | Varshavsky ....... G06F 17/30864 707/732 |
| 2011/0093295 A1 | 4/2011 | Mankad et al. |
| 2011/0106589 A1 | 5/2011 | Blomberg et al. |
| 2011/0112852 A1* | 5/2011 | Ware .................... G06F 19/363 705/2 |
| 2011/0270632 A1 | 11/2011 | Manning et al. |
| 2011/0276396 A1 | 11/2011 | Rathod |
| 2012/0072232 A1 | 3/2012 | Frankham et al. |
| 2012/0123223 A1* | 5/2012 | Freeman ............... G16H 40/63 600/301 |
| 2012/0284332 A1* | 11/2012 | Pradeep ............. G06Q 30/0269 709/204 |
| 2013/0036080 A1 | 2/2013 | Kane-Esrig |

OTHER PUBLICATIONS

Corley et al., "Monitoring Influenza Trends Through Mining Social Media," Univer., North Texas Health Center; pp. 1-7 (2008).
English et al., "Transforming Clinical Research in the United States: Challenges and Opportunities, Forum on Drug Discovery, Development, and Translation," *Institute of Medicine*; pp. 1-123 (2010).
Etiger et al., "Massive Social Network Analysis: Mining Twitter for Social Good," *The 39th International Conference on Parallel Processing*, pp. 1-11 (2010).
Kleiber, "Document Classification Through Data Mining Social Media Networks," *Stetson University*, pp. 1-37 (Nov. 13, 2009).
Liu et al., "Mining Data Records in Web Pages," *KDD '03 Proceedings of the Ninth ACM SIGKDD International Conference on Knowledge Discovery and Data Mining*, pp. 1-10 (2000).
Liu, et al., "Mining Topic-Specific Concepts and Definitions on the Web," *WWW'3 03 Proceedings of the 12th International Conference on World Wide Web*, pp. 1-10 (May 2003).
Liu, "Sentiment Analysis and Subjectivity," *Handbook of Natural Language Processing*, Second Edition, pp. 1-38 (2010).
OPDP, "Guidance for Industry," pp. 1-15 (Dec. 2011).
Wicks et al., "Accelerated clinical discovery using self-reported patient data collected online and a patient-matching algorithm," *Nature Biotechnology*, 29(5):411-416 (May 11, 2011).
Office Action from the United States Patent & Trademark Office in U.S. Appl. No. 13/549,890, dated May 22, 2013.
Office Action from the United States Patent & Trademark Office in U.S. Appl. No. 13/549,890, dated Sep. 17, 2013.
Search Report issued in corresponding International Application No. PCT/US2013/050756, dated Nov. 5, 2013, 4 pages.
Office Action from the United States Patent & Trademark Office in U.S. Appl. No. 13/549,890, dated Mar. 3, 2014.
Office Action from the United States Patent & Trademark Office in U.S. Appl. No. 13/549,890, dated Jun. 27, 2014.
Office Action from the United States Patent & Trademark Office in pending U.S. Appl. No. 13/543,044, dated Sep. 26, 2014.
Office Action from the United States Patent & Trademark Office in U.S. Appl. No. 13/549,890, dated Feb. 11, 2015.
Office Action from the United States Patent & Trademark Office in U.S. Appl. No. 13/549,890, dated Jun. 30, 2015.
Office Action from the United States Patent & Trademark Office in pending U.S. Appl. No. 13/543,044, dated Mar. 26, 2015.
Office Action from the United States Patent & Trademark Office in pending U.S. Appl. No. 13/543,044, dated Oct. 7, 2015.
Notice of Allowance from the United States Patent & Trademark Office in U.S. Appl. No. 13/549,890, dated Dec. 8, 2015.
Office Action from the United States Patent & Trademark Office in pending U.S. Appl. No. 13/543,044, dated Jun. 6, 2016.

* cited by examiner

| | 700 |
|---|---|
| Symptom 702 | Fever |
| Possible Causes 704 | A |
| | B |
| | C |
| | D |
| | E |
| | ... |
| Suggested Treatments 706 | 1 |
| | 2 |
| | 3 |
| | |

FIG. 7

| | |
|---|---|
| Patient ID 802 | |
| Social ID 804 | |
| General Practitioner 806 | |
| Specialist 808 | |
| Hospital 810 | |
| Emergency Responder 812 | |
| Family 814 | |
| Friend 816 | |
| Routine Contact 818 | |
| Regular Activity 820 | |
| Other 822 | |

SYSTEM AND METHOD OF APPLYING STATE OF BEING TO HEALTH CARE DELIVERY

CROSS REFERENCE TO RELATED APPLICATION

This is a continuation of U.S. patent application Ser. No. 13/549,890, filed Jul. 16, 2012, of which is hereby incorporated by reference.

BACKGROUND

Health care is delivered in many forms, venues and by different providers. Venues range from hospitals and their emergency facilities, outpatient offices, day surgical centers, storefront 'doc in a box', community health centers, concierge service including home visits and by self-help. Providers range from physicians and surgeons with different primary or specialized training, nurses inclusive of advanced practice, registered or license practical, physician assistants, physical therapists, speech therapists and occupational therapists. In addition, self-directed Internet/network-based medical assistance and over-the-counter (OTC) treatments are utilized. These various forms of delivery differ significantly in terms of cost of care, intensity of care, and availability of care. For example, a visit to an emergency room can be very expensive as compared to other forms of treatments. Similarly, a visit to a doctor or other provider typically costs more than using OTC treatments. Of course, cost of care is not always the most important factor for selecting a proper treatment. Other important factors that may affect the selection of a treatment include likelihood of success, adverse effects, whether a treatment is immediately available, etc. Overall, health care delivery and treatments should effectively treat the conditions of a patient in a timely manner.

Unless incapacitated, a person can often freely choose the form of treatment for an ailment, injury or medical problem. Yet when a person does not understand their symptoms or condition, he or she runs a higher risk of choosing a wrong treatment, such as a more expensive but unnecessary one, or worse, may fail to appreciate the severity of their condition. For example, a person suffering a stomachache or a pain in the upper abdomen may not appreciate they have indigestion, which will pass in a relatively short time. In such an instance the person could take an over-the-counter treatment or simply rest, but instead sees a doctor or rushes to the emergency room. Or, at the other extreme, the person has a string of stomachaches indicating a more serious condition, but continually dismisses the stomachaches as gas.

Also of concern is the lack of guidance when people self-medicate or self-treat. For example, when a person takes an OTC treatment, he or she may not be aware of contraindicated substances for that treatment that could lead to serious or even deadly interactions. In such an instance, a person experiencing a symptom may need immediate medical attention.

Certain factors reduce the efficiency of the health care system when a person is in need of treatment. One factor is the relevant healthcare knowledge of a person, i.e., whether a person has or lacks sufficient knowledge to determine the proper health care protocol. People often do not recognize what symptoms indicate a need for urgent care, care that can be scheduled, or can be addressed with self-help. Another factor is a person's medical history may not be readily accessible by a healthcare professional, for example at the point of emergency or urgent care. A healthcare provider may eventually obtain a patient's records, but not in time to contribute to diagnosis and treatment in an urgent care situation. In such an instance, when a patient is incapacitated the accuracy of the patient's medical history cannot be confirmed. Without accurate medical history for the patient, a health care provider may fail to make a correct diagnosis or may misdiagnose a particular patient with unusual baseline measurements as having symptoms as normal, when their unique medical history would reveal a problem.

Yet another factor is that the person can be confused about what causes a symptom and exaggerates the need for urgent care. Although people may not intend to conceal or misrepresent information when talking with a caregiver, caregivers often find a substantial amount of inaccuracy and discrepancy in their patients' self-described symptoms.

Various technologies have been implemented to improve the efficiency and accuracy of the health care delivery. For example, electronic health records are used to make a patient's medical history readily available to a caregiver. Remote monitoring systems and devices can monitor a person's vital statistics, such as temperature, blood pressure, and electrocardiograms (EKG) and forward the monitoring results to associated servers in real-time; such devices can be stand alone devices or enabled as applications in other devices, such as smart phones or even smart watches. Internet/network-based clinical decision support systems such as diagnozit.com, niaclin.com, medgle.com, and simulconsult.com have been developed to help patients or health care providers with diagnoses and treatments. For example, the systems can remind clinicians and providers what to look for during patient encounters, make sure not to duplicate diagnostic testing or treatments, detect and avoid contraindicated treatments, and instruct patients how to self-treat.

SUMMARY

Conventional remote or automated health care delivery systems do not take account of person's subjective state of being, such as, for example, mental state, mood, sense of elation, depression, appetite, desire, self-perceived ability to be able to or not able to perform tasks, etc. Conventional health care delivery systems do not utilize the vast information that is associated with a person that is available through the Internet, a network, or some interworking of networks (referred to hereafter as "internet"), as for example may be available on social networks such as Twitter, Facebook, Google+, Reddit, etc. Conventional health care systems also fail to make use of or recognize data from individual subjects, and instead use statistically obtained reference data derived from the general public and apply it to an individual subject.

Accordingly, disclosed is a system and a method that provide personalized health care, that collect temporal and longitudinal cross-section of measurement data of a subject's health parameters, monitor real-time medical telemetry, and infer subject's subjective state of being from at least one social network. The system and method can correlate the subjective state of being and symptom data from multiple subjects and can correctly route a communication to the appropriate entity when a subject is in need of medical attention. The system and method can further communicate important health data about a subject without violating laws and regulations governing sensitive or protected health care information.

An embodiment of the present disclosure is directed to a system for assisting a patient to select a proper form of treatment. The system includes an interface for a monitoring section that monitors a health status of the patient; an inference section that infers additional medical information about the patient based on information about the patient from at least one social network; a patient database that stores a patient's information; and a symptom engine that stores symptom data of medical conditions. The inference section processes the health status and the medical information and compares it against symptom data stored in the symptom engine to determine a treatment response.

According to another embodiment of the present disclosure, the inference section further infers a medical trend as the medical information based on a symptom of the patient and information obtained through the at least one social network.

According to another embodiment of the present disclosure, the inference section further infers a state of being of the patient as the medical information based on a symptom of the patient and information obtained through the at least one social network.

According to another embodiment of the present disclosure, the inference section obtains information from the patient's network from at least one social network.

According to another embodiment of the present disclosure, the inference section correlates symptoms and states of being from multiple patients.

According to another embodiment of the present disclosure, the monitoring section comprises a mobile wireless monitoring device.

According to another embodiment of the present disclosure, the system further includes an interface with an aggregation component configured to aggregate information from the monitoring section about the health status of the patient.

According to another embodiment of the present disclosure, the system further contacts a health care provider when a medical treatment is needed.

Another embodiment of the present disclosure is directed to a method for assisting a patient to select a proper form of treatment. The method includes remotely monitoring a health status of the patient; inferring medical information about the patient based on information of the patient obtained from the at least one social network; storing the patient's information; and storing symptoms of medical situations. The inferring includes applying the health status and the medical information against the stored symptoms to determine a treatment response.

According to another embodiment of the present disclosure, the inferring further comprises inferring a medical trend as the medical information based on a symptom of the patient and information obtained through at least one social network.

According to another embodiment of the present disclosure, the inferring further comprises inferring a state of being of the patient as the medical information based on a symptom of the patient and information obtained through the at least one social network.

According to another embodiment of the present disclosure, the inferring further comprises obtaining information the patient's network about the patient from the at least one social network.

According to another embodiment of the present disclosure, the inferring comprises correlating symptoms and state of being from multiple patients.

According to another embodiment of the present disclosure, the monitoring comprises using a mobile wireless monitoring device.

According to another embodiment of the present disclosure, the method further includes receiving aggregated information about the health status of the patient from an aggregation component that aggregates the health status information from the patient.

According to another embodiment of the present disclosure, the method further includes contacting a health care provider when a medical treatment is needed.

Another embodiment of the present disclosure is directed to a storage medium storing a program that, when executed, causes a processor to execute a method, as set forth in the present disclosure, for assisting a patient to select a proper form of treatment.

Another embodiment of the present disclosure is directed to a device comprising an aggregation component configured to monitor a health status of a patient and aggregate information about the health status of the patient. The device further comprises an interface with a system which includes an inference section that infers additional medical information about the patient based on information about the patient from at least one social network; a patient database that stores patient's information; and a symptom engine that stores symptom data of medical conditions. The inference section processes the health status and the medical information and compares it against symptom data stored in the symptom engine to determine a treatment response.

According to another embodiment of the present disclosure, the aggregation component is connected with the patient database and the symptom engine via a network.

According to another embodiment of the present disclosure, the aggregation component comprises an interface that monitors the heath status of the patient, and a communication unit that communicates with the inference engine.

According to another embodiment of the present disclosure, the aggregation component comprises a device selected from an advanced mobile wireless device such as a mobile phone, a tablet, or a wireless radio base station.

According to another embodiment of the present disclosure, the aggregation component normalizes readings of at least one monitoring device.

According to another embodiment of the present disclosure, the aggregation component is configured to filter out insignificant information to reduce the amount of network traffic.

According to another embodiment of the present disclosure, the aggregation component is configured to otherwise preprocess the information to reduce load on the server or improve data accuracy.

Another embodiment of the present disclosure is directed to a system for assisting a patient to select a proper form of treatment. The system includes an application section hosted by the patient that monitors a health status of the patient, aggregates information about the health status of the patient, and obtains additional medical information about the patient based on information about the patient from at least one social network; a storage section coupled to the application section that stores a patient's information; and a symptom engine that stores symptom data of medical conditions. The application section processes the health status and the medical information and compares it against symptom data stored in the symptom engine to determine a treatment response.

According to another embodiment of the present disclosure, the storage section is locally connected with the application section.

According to another embodiment of the present disclosure, the application section is connected with the symptom engine via a network.

According to another embodiment of the present disclosure, the application section comprises a smart phone or a tablet.

According to another embodiment of the present disclosure, the application section comprises a device selected from a smart phone, a tablet, a smart watch, or a wireless radio base station.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like.

The above and other objects, features, and advantages of various embodiments as set forth in the present disclosure will be more apparent from the following detailed description of embodiments taken in conjunction with the accompanying drawings.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 7 illustrates a record 700 of the symptom database engine 112 according to an embodiment of the present disclosure.

FIG. 8 illustrates a record 800 of the patient database 114 according to an embodiment of the present disclosure.

DETAILED DESCRIPTION

It will be appreciated by those ordinarily skilled in the art that the foregoing brief description and the following detailed description are exemplary (i.e., illustrative) and explanatory of the subject matter as set forth in the present disclosure, but are not intended to be restrictive thereof or limiting of the advantages that can be achieved by the present disclosure in various implementations. Additionally, it is understood that the foregoing summary and ensuing detailed description are representative of some embodiments as set forth in the present disclosure, and are neither representative nor inclusive of all subject matter and embodiments within the scope as set forth in the present disclosure. Thus, the accompanying drawings, referred to herein and constituting a part hereof, illustrate embodiments of this disclosure, and, together with the detailed description, serve to explain principles of embodiments as set forth in the present disclosure.

Further, it will be understood that an ordinarily skilled artisan will be familiar with technology for information extraction, relation generation, data mining, summarization, sentiment analysis, similar document detection, databases, information retrieval, machine translation, cross language retrieval, and natural language processing systems and techniques. Exemplary publications describing material known to ordinarily skilled artisans, the entirety of each of which are incorporated by reference herein, include:

*Introduction to Information Retrieval*, Manning, Raghavan, and Schütze, Cambridge University Press, 2008.

*Data Mining: Concepts and Techniques*, Morgan Kaufmann, Han and Kamber, 2006

Database *Systems Concepts*, McGraw Hill, Silberschatz, Korth, and Sudarshan, 2010.

Graph-*based Natural Language Processing and Information Retrieval*, Mihalcea and Radev, Cambridge University Press, 2011.

*Mining the Social Web*, Mathew A. Russell, ISBN: 9781449388348, O'Reilly Media, Inc., 2011.

The entire disclosure of U.S. Application 61/505,402, "SYSTEM AND METHOD FOR PERFORMING PHARMACOVIGILANCE," is incorporated herein by reference.

Figure 1A:
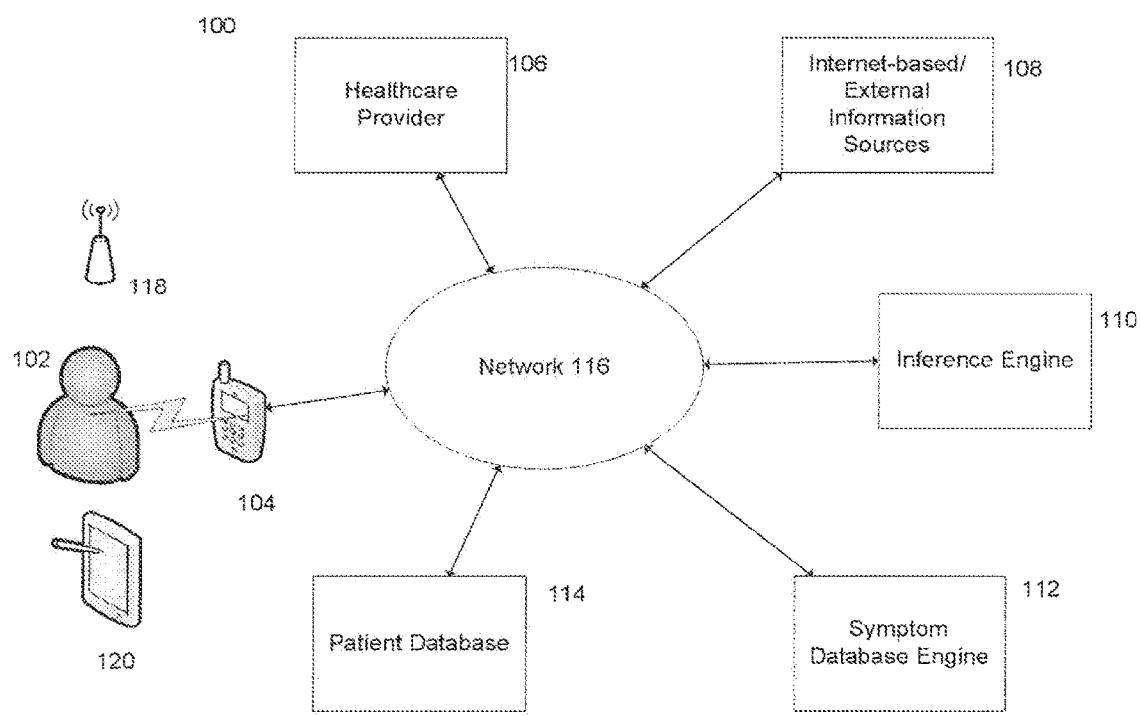
FIG. 1a illustrates the system according to an embodiment of the present disclosure.

FIG. 1a illustrates a system for selecting a course of treatment for an individual according to an embodiment as set forth in the present disclosure. An individual or user is also referred to as patient throughout this disclosure; as will be appreciated, patients as used herein not only refer to subjects actually receiving or in need of health care services or otherwise under the care of a health care professional, but also include subjects who are potential health care consumers, subjects who self-treat, or users who otherwise interact with embodiments as described herein. The system 100 includes interfaces and operative connections between a patient or user 102, a patient monitoring component 104, an at least one health care provider 106, internet-based information sources 108, an inference engine 110, a symptom database engine 112, a patient database 114, a network 116, a communication device 118, and a storage device 120.

The inference engine 110 is configured to receive real-time telemetry and patient data about the health of the patient. When the patient 102 has a symptomatic or medical event, the patient or user acting on his or her behalf may initiate a communication with the inference engine 110 by using the communication device 118. As used herein, a symptomatic or medical event refers broadly to any event that possibly involves the art of medicine or healthcare, that is, the art or science of restoring or preserving health or due physical condition by any means, including but not limited to drugs, surgical operations or appliances, or manipulations, as well as any disciplines that provide or treat or restore health, including but not limited to medicine proper, surgery, obstetrics, dentistry, psychology, psychiatry, physical therapy, speech therapy, occupational therapy, alternative medicine, and so on. The monitoring component 104 may also be configured to notify the inference engine 110 about the medical event, allow the patient to do so, or both.

The monitoring component 104 is configured to monitor the patient 102 and send real-time telemetry about the patient's health (e.g., vital statistics such as temperature, heartbeat, pacemaker data, etc.) to identified or desired recipients. The inference engine 110 can also be configured to receive data about a patient's immediate environment (e.g., temperature from an intelligent energy device such as smart thermostat, GPS location data from a device so enabled, weather, etc.). The inference engine 110 is configured to identify the patient 102 by using the information stored in the patient database 114. The inference engine 110 further obtains data about the patient 102 from one or more of internet-based information sources 108 and extracts state of being information about the patient, which the inference engine 110 is configured to analyze and identify a proper course of treatment for the patient.

The inference engine 110 assembles all the data it receives about the health status of the patient 102 into a current health status and compares the patient's current health status data against the information included in the symptom database engine 112. Such an application will result in a determination of a proper form of health care and/or course of treatment and will forward a treatment response message to the patient 102. Then, the inference engine 110 transmits a message including information about the proper course of treatment back to the patient 102 or reroutes the communication from the patient 102 to a suitable health care provider 106 or both. A storage device 120 stores all the communications between the patient 102 and the system 100, and can include a medical history of the patient 102, and any other health related information of the patient 102 to which it has accessed. In certain embodiments, health care data may be transmitted from health care providers and affiliates thereof that have a duty to keep personal medical information secure and private in accord with legal regulatory schemes, such as rules and regulations promulgated pursuant to The Health Insurance Portability and Accountability Act (HIPAA). In such instances, the system 100 can be configured such that components handling communication and storage on behalf of institutions and entities having such duties communicate properly secured in accord with the appropriate regulations using data security techniques and system components known in the art.

The monitoring component 104 may be a single device or a distributed system. For example, a monitoring component 104 can be included in or designed for a cell-phone-based device, applications on a smart phone or a specially designed portable or wearable, device configured to monitoring the health status of the patient 102 wherever the patient carries the device. Vital statistics such as temperature, blood pressure, heart rate, blood sugar, prescription compliance, or even metabolism of the patient 102 can be continuously monitored and transmitted to the inference engine 110 through the network 116. The portable device stores the monitoring results on the storage device 120, which may be an internal component of the portable device. Non-limiting, exemplary cell-phone based health-monitoring components include CellCheck and Cell Phone Home Monitoring Solutions and sensors provided by GENTAG, INC. A distributed monitoring component can also include a system or device such as an intelligent energy device that monitors the living situation and environment of the patient, such as for example the temperature, the humidity, and chemical and/or biological composition in the air of the living place. It is noted that the communication device 118 and the storage device 120 may be included in the monitoring system 104 or may be devices independent from the monitoring system 104.

As noted above, personal medical information can be subject to strict regulations, such as Health Insurance Portability and Accountability Act (HIPAA) in the U.S., to protect the privacy of the patient. Because patient's telemetry data as well as patient's own search keywords or comments on social networks could be treated as personal medical information, the system is designed to comply with the requirements under HIPPA. For example, in an embodiment the system gathers health data, including health status and state of being data, from patients or from various sources with their permission. While the system is configured such that the inference engine 110 provides this information to health care providers, it may not itself be a health care provider nor an affiliated entity, and thus may not be under a duty to maintain the patient's data in accordance with HIPPA requirements. However, as noted above, any components of the system can be configured to meet with HIPPA compliance standards as needed.

As used herein, the network 116 should be broadly construed to include any one or more of a number of types of networks that may be created between devices using an internet connection, a LAN/WAN connection, a telephone connection, a wireless connection, a short message system (SMS), and so forth. Each of the terminals, servers, and systems may be, for example, a server computer or a client computer or client device operatively connected to network 116, via bi-directional communication channel, or interconnector, respectively, which may be, for example a serial bus such as IEEE 1394, or other wire or wireless transmission medium such as 3G or 4G networks. The terms "coupled with," "operatively connected," "operatively coupled," and "communicatively coupled", as used herein, mean that the elements so connected or coupled are adapted to transmit and/or receive data, or otherwise communicate. This connection/coupling may or may not involve additional transmission media, or components, and may be within a single module or device or between the remote modules or devices. The terms "connected" and "coupled" thus include directly connected to or indirectly connected through one or more intermediate components. Such intermediate components may include both hardware and software based components.

It should be appreciated that a typical system can include a large number of connected computers (e.g., including server clusters), with each different computer potentially being at a different node of the network 116. The network, and intervening nodes, may comprise various configurations and protocols including the internet, World Wide Web, intranets, virtual private networks, wide area networks, local networks, private networks using communication protocols proprietary to one or more companies, Ethernet, WiFi and HTTP, cloud and cloud based services, and various combinations of the foregoing. Such communication may be facilitated by any device capable of transmitting data to and from other computers, such as modems (e.g., dial-up, cable or fiber optic) and wireless interfaces.

The terminals, servers, devices, and systems are adapted to transmit data to, and receive data from, each other via the network 116. The terminals, servers, and systems typically utilize a network service provider, such as an Internet Service Provider (ISP) or Application Service Provider (ASP) (ISP and ASP are not shown) to access resources of the network 116.

Although each of the above described terminal, server, and system may comprise a full-sized personal computer, the system and method may also be used in connection with mobile devices capable of wirelessly exchanging data with a server over a network such as the internet. For example, a terminal, client device or user device may be a wireless-enabled PDA such as an iPhone, an Android enabled smart phone, a Blackberry phone, an I'm Watch, an iPad, or another internet-capable wireless device.

Figure 1B:
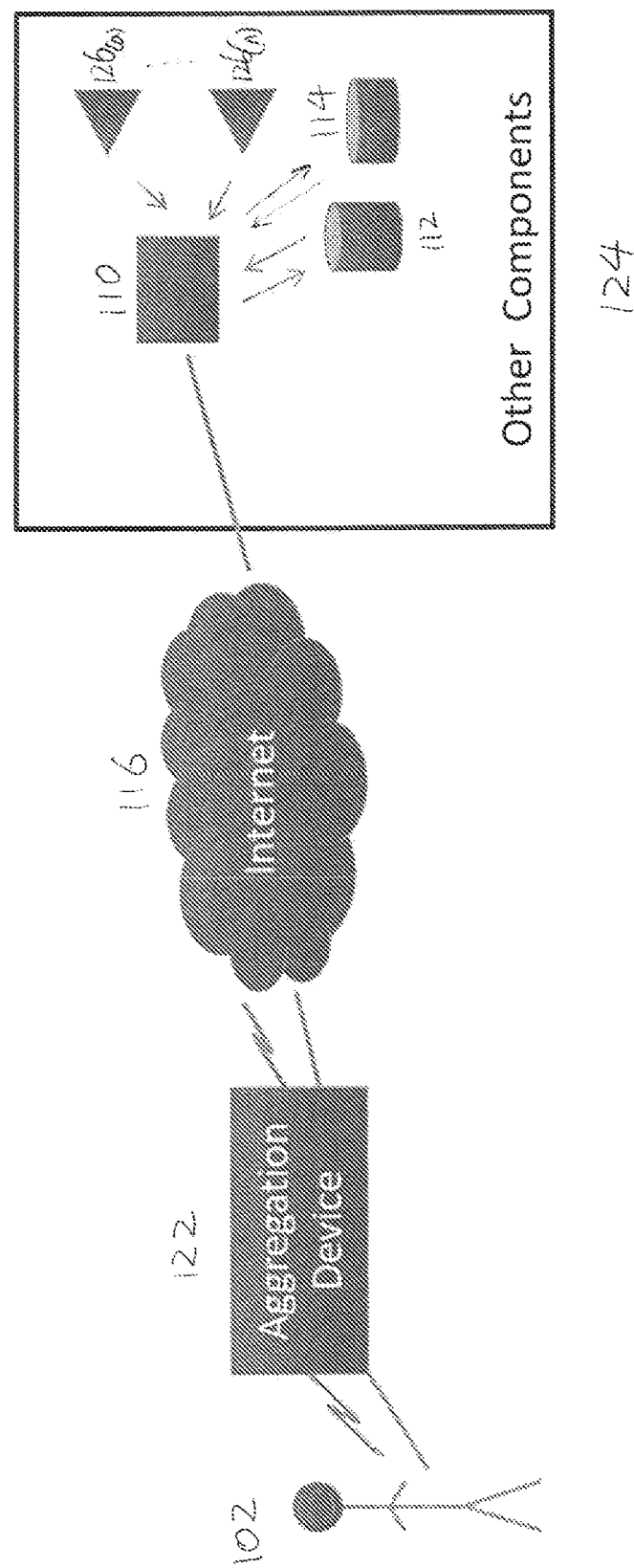
FIG. 1b illustrates a system according to another embodiment of the present disclosure.

FIG. 1b illustrates another embodiment of a system for selecting a course of treatment for an individual according to another embodiment as set forth in the present disclosure. As illustrated in FIG. 1b, the system 100b comprises an aggregation device 122, which represents an integrated multifunctional device between the patient 102 and the rest of the system such as the internet 116 and external components 124 of the system 100b. The external components 124 includes the internet-based information sources 108, the inference engine 110, the symptom database engine 112, and the patient database 114 that are not hosted and managed by the patient 102.

The aggregation device 122 may be hosted and managed by the patient 102 rather than by a third party. The aggregation device 122 may be formed by the combination of the monitoring component 104, the communication device 118, and the storage device 120. Alternatively, the aggregation device 122 may include more or less components depending on the required functions. The aggregation device 122 collects real-time medical telemetry from body sensors, for example through a personal area network (PAN) such as Bluetooth or a wired network, such as via a USB device. Non-limiting examples of an aggregation device 122 comprise an advanced mobile phone, a tablet, a wireless radio base station such as a Qualcomm 2net Hub™, or other medical telemetry device. The aggregation device 122 is configured to send a stream of medical data to the inference engine 110 included in other components 124 over a wireless local area network to a router or via a wired local area network to a router. The external components 124 may include the inference engine 110, the patient database 114, the symptom database engine 112, and various inputs from patient related information sources 126(a) to 126(n). The router forwards the packets to the inference engine 110 over the network 116. Alternatively, the aggregation device 122, if for example it is a mobile phone or a Public Land Mobile System device, can send the data using 2.5G, 3G, 4G, or other relevant wireless technology through a service provider, which will forward the packets to the network 116, which will forward the packets to the inference engine 110. Besides passing through measurements streaming from different sensors, the aggregation device 122 may also normalize the readings and aggregate the messages to the inference engine 110. According to an embodiment of the present disclosure, the aggregation may result in only sending significant changes in readings, thus reducing the amount of traffic through the network. In addition, the aggregation device may preprocess or analyze the data prior to sending a summary to the inference engine 110, thus reducing the load on the inference engine.

Figure 1C:
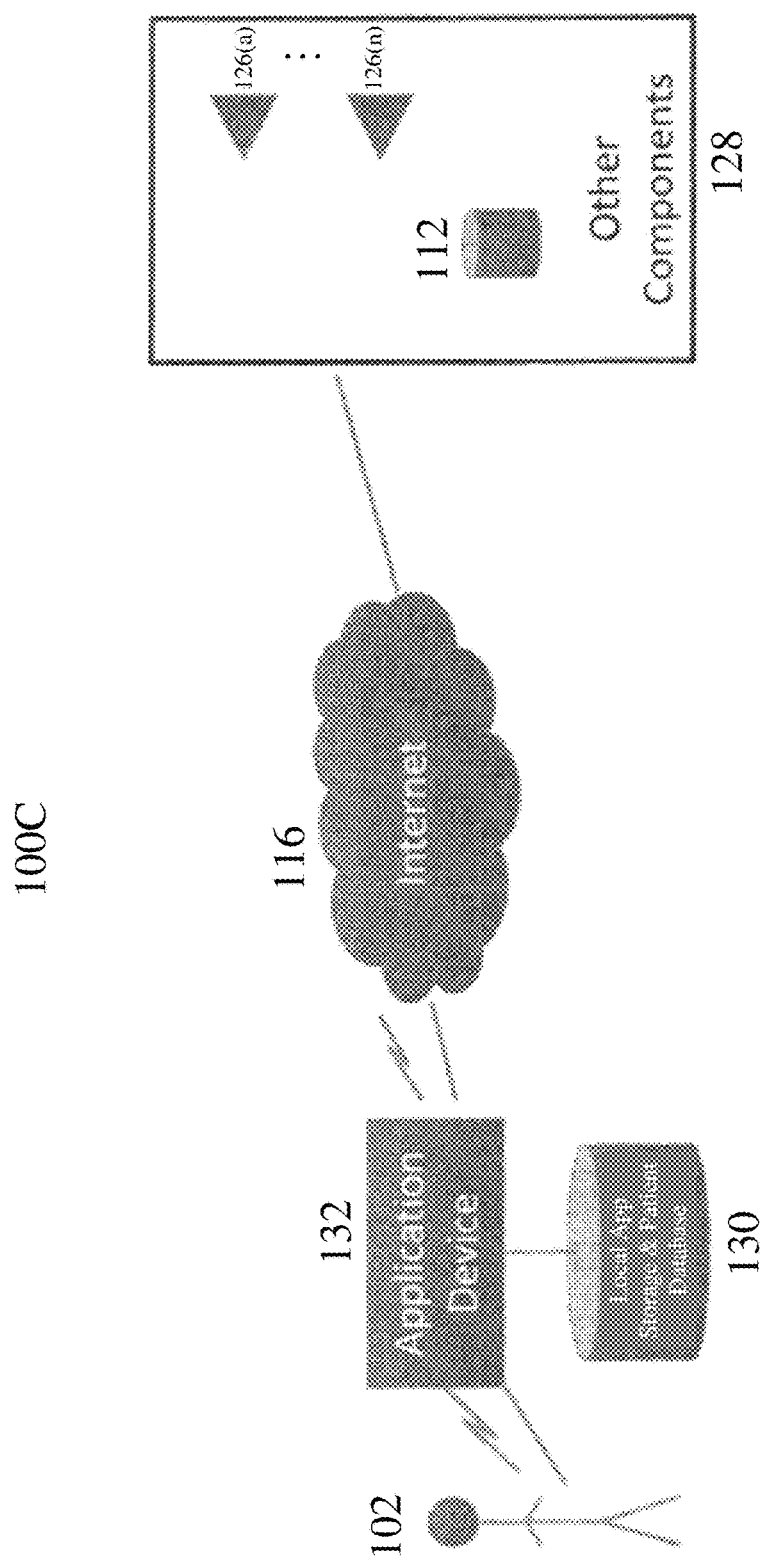
FIG. 1c illustrates a system according to another embodiment of the disclosure.

FIG. 1c illustrates a system 100c for selecting a course of treatment for an individual according to another embodiment as set forth in the present disclosure. As will be noted, the embodiment of FIG. 1c does not include the inference engine 110 or the remotely located patient database 114. Also shown in FIG. 1c, another difference is an application device 132 and an application storage and patient database 130.

The application device 132 takes real-time medical telemetry, normalizes the telemetry, and analyzes the collected information. The application device 132 makes queries and receives various inputs from internet-based patient information sources 126(a) to 126(n), which may offer medical trend analysis, state of being of the patient 102, and the current and past protocols in use by the patient 102. The application device 132 then queries the symptom database engine 112 using the patient's parameters to determine the best matching outcomes and proposed actions. The application device 132 then can interact with the patient 102 and healthcare providers (not shown in FIG. 1c).

An application storage and patient database 130 stores not only the patient data but also stores the applications used by the application device 132. For example, in an embodiment, the application device 132 retrieves stored software applications and patient data from a local application storage and patient database 130 and also stores the updates of those applications and data. In another exemplary embodiment (not shown), the application storage and patient database 130 can be remotely located from the patient 102 and application device 132, and the application can be stored in the application storage and patient database 130 may be dynamically downloaded from another, non-local source external to the patient 102 each time the application is executed. In another exemplary embodiment, the application device retrieves or installs software applications from a CD-ROM.

The application device 130 and the local application storage and patient database 130 may be hosted and managed by the patient 102. Accordingly, the system 100c as illustrated in FIG. 1c has the benefits of having all of the patient's data stored in the patient's application device 132 and the local application storage and patient database 130. This eliminates many of the issues associated with the long-term storage of patient medical data by non-patient entities, such as those who have a duty to secure and keep private personal medical information. Moreover, this affords the patient with the useful benefit of having access to and total control over their own medical records.

Figure 2A:
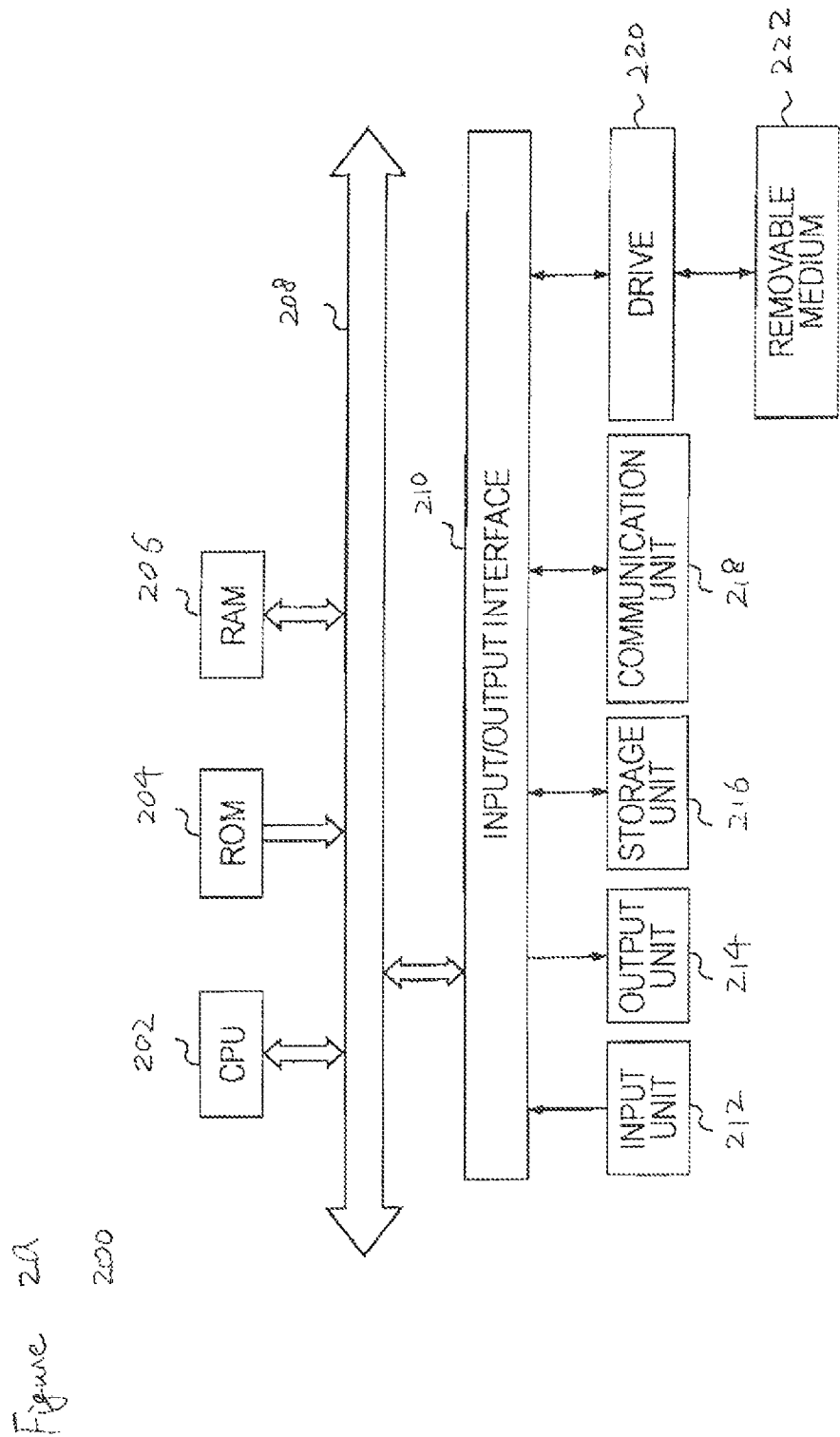
FIG. 2a illustrates an exemplary structure of a server, system, or a terminal according to an embodiment of the present disclosure.

FIG. 2a illustrates an exemplary structure of a server, system, or a terminal according to an embodiment. The exemplary server, system, or terminal 200 includes a CPU 202, a ROM 204, a RAM 206, a bus 208, an input/output interface 210, an input unit 212, an output unit 214, a storage unit 216, a communication unit 218, and a drive 220. The CPU 202, the ROM 204, and the RAM 206 are interconnected to one another via the bus 208, and the input/output interface 210 is also connected to the bus 208. In addition to the bus 208, the input unit 212, the output unit 214, the storage unit 216, the communication unit 218, and the drive 220 are connected to the input/output interface 210.

The CPU 202, such as an Intel Core™ or Xeon™ series microprocessor or a Freescale™ PowerPC™ microprocessor, executes various kinds of processing in accordance with a program stored in the ROM 204 or in accordance with a program loaded into the RAM 206 from the storage unit 216 via the input/output interface 210 and the bus 208. The ROM 204 has stored therein a program to be executed by the CPU 202. The RAM 206 stores as appropriate a program to be executed by the CPU 202, and data necessary for the CPU 202 to execute various kinds of processing. The CPU 202 may include multiple processors such as ASICs, FPGAs, GPUs, etc.

A program may include any set of instructions to be executed directly (such as machine code) or indirectly (such as scripts) by the processor. In that regard, the terms "instructions," "steps" and "programs" may be used interchangeably herein. The instructions may be stored in object code format for direct processing by the processor, or in any other computer language including scripts or collections of independent source code modules that are interpreted on demand or compiled in advance. Functions, methods and routines of the instructions are explained in more detail below.

The input unit 212 includes a keyboard, a mouse, a microphone, a touch screen, and the like. When the input unit 212 is operated by the user, the input unit 212 supplies an input signal based on the operation to the CPU 202 via the input/output interface 210 and the bus 208. The output unit 214 includes a display, such as an LCD, or a touch screen or a speaker, and the like. The storage unit 216 includes a hard disk, a flash memory, and the like, and stores a program executed by the CPU 202, data transmitted to the terminal 200 via a network, and the like.

The communication unit 218 includes a modem, a terminal adaptor, and other communication interfaces, and performs a communication process via the networks of FIG. 1.

A removable medium 222 formed of a magnetic disk, an optical disc, a magneto-optical disc, flash or EEPROM, SDSC (standard-capacity) card (SD card), or a semiconductor memory is loaded as appropriate into the drive 220. The drive 220 reads data recorded on the removable medium 222 or records predetermined data on the removable medium 222.

One skilled in the art will recognize that, although the data storage unit 216, ROM 204, RAM 206 are depicted as different units, they can be parts of the same unit or units, and that the functions of one can be shared in whole or in part by the other, e.g., as RAM disks, virtual memory, etc. It will also be appreciated that any particular computer may have multiple components of a given type, e.g., CPU 202, Input unit 212, communications unit 218, etc.

An operating system such as Microsoft Windows 7®, Windows XP® or Vista™, Linux®, Mac OS®, or Unix® may be used by the terminal. Other programs may be stored instead of or in addition to the operating system. It will be appreciated that a computer system may also be implemented on platforms and operating systems other than those mentioned. Any operating system or other program, or any part of either, may be written using one or more programming languages such as, e.g., Java®, C, C++, C#, Visual Basic®, VB.NET®, Perl, Ruby, Python, or other programming languages, possibly using object oriented design and/or coding techniques.

Data may be retrieved, stored or modified in accordance with the instructions. For instance, although the system and method is not limited by any particular data structure, the data may be stored in computer registers, in a relational database as a table having a plurality of different fields and records, XML documents, flat files, etc. The data may also be formatted in any computer-readable format such as, but not limited to, binary values, ASCII or Unicode. The textual data might also be compressed, encrypted, or both. By further way of example only, image data may be stored as bitmaps comprised of pixels that are stored in compressed or uncompressed, or lossless or lossy formats (e.g., JPEG), vector-based formats (e.g., SVG) or computer instructions for drawing graphics. Moreover, the data may comprise any information sufficient to identify the relevant information, such as numbers, descriptive text, proprietary codes, pointers, references to data stored in other memories (including other network locations) or information that is used by a function to calculate the relevant data.

It will be understood by those of ordinary skill in the art that the processor and memory may actually comprise multiple processors and memories that may or may not be stored within the same physical housing. For example, some of the instructions and data may be stored on removable memory such as a magneto-optical disk or SD card and others within a read-only computer chip. Some or all of the instructions and data may be stored in a location physically remote from, yet still accessible by, the processor. Similarly, the processor may actually comprise a collection of processors which may or may not operate in parallel. As will be recognized by those skilled in the relevant art, the terms "system," "terminal," and "server" are used herein to describe a computer's function in a particular context. A terminal may, for example, be a computer that one or more users work with directly, e.g., through a keyboard and monitor directly coupled to the computer system. Terminals may also include a smart phone device, a personal digital assistant (PDA), thin client, or any electronic device that is able to connect to the network and has some software and computing capabilities such that it can interact with the system. A computer system or terminal that requests a service through a network is often referred to as a client, and a computer system or terminal that provides a service is often referred to as a server. A server may provide contents, content sharing, social networking, storage, search, or data mining services to another computer system or terminal. However, any particular computing device may be indistinguishable in its hardware, configuration, operating system, and/or other software from a client, server, or both. The terms "client" and "server" may describe programs and running processes instead of or in addition to their application to computer systems described above. Generally, a (software) client may consume information and/or computational services provided by a (software) server.

Figure 2B:
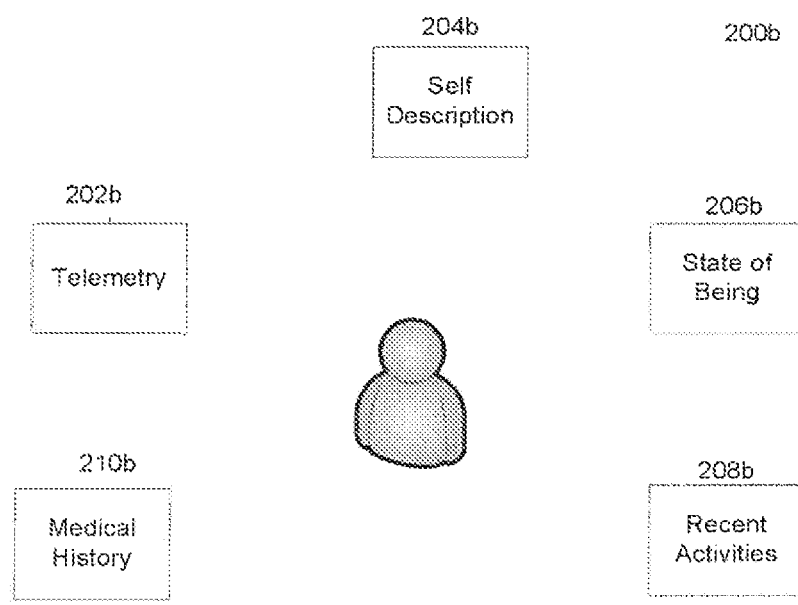
FIG. 2b illustrates exemplary categories that may be used to classify the medical status information according to an embodiment of the present disclosure.

Medical status of a patient comprises a wide scope of information about the patient as long as the information plays a role in determining a medical treatment of the patient. FIG. 2b illustrates exemplary categories that may be used to classify the medical status information according to an embodiment of the present disclosure. The medical status information 200b for a patient may be grouped into a plurality of categories including telemetry 202b, self-description 204b, state of being 206b, recent activities 208b, and medical history 210b. The telemetry 202b comprises real-time measurements of a patient's health status as described herein such as body temperature, weight, blood pressure, heart rate, prescription compliance, EKG, metabolism, bowel movement frequency, urine production, etc. The telemetry 202b may also comprise the geographical location information of the patient. The telemetry 202b may also comprise real-time measurements of the patient's living place such as ambient temperature, chemical composition of air, biological substance in the air, humidity, etc. The self-description data 204b comprises any information about patient's symptoms and possible causes expressed by the patient through any communication such as that recorded in person, over the phone, via e-mail or SMS messaging, and via one or more social networks. The state of being data 206b comprises information about patient's state of mind, mood, sense of elation, depression, appetite, desire, self-perceived ability to be able to or not able to perform tasks, feelings, etc. The recent activities data 208b comprise information about patient's recent diet, social events, errands, frequently visited locations, etc. The medical history 210b comprises information about patient's current prescription (s), current medical treatment(s), allergies, past medical treatments, family disease, etc. These categories of information are not completely isolated and separated from each other. Information may be classified into multiple categories or information in one category may be used to infer information in another category. It is also noted that the list of categories in FIG. 2b is not exhaustive and a person of ordinary skill in the art may add new categories, remove certain categories, or change the names of these categories.

Data from any of these categories can be obtained from multiple sources, as for example, frequent locations for the patient may be obtained from a social network "check-in," a GPS device with the patient (e.g., in a smart phone), via a communication from the patient, the patient's favorite and frequently visited coffee shop keeper, and so on. For example, the medical status information 200b of a patient can be obtained from multiple sources. Patients typically offer self-descriptions 204b and recent activities 208b. Telemetry 202b can obtained from monitoring components. Medical history 210b may be given by the patient or obtained from patient's doctors. According to an embodiment of the present invention, the state of being 206b and recent activities 208b may be obtained through at least one social network or one or more internet hosted sites used by the patient such as Yahoo, Google+, Twitter, Facebook, YouTube, Foursquare, Docshare, or Blogs. Such information can also be obtained via communication with frequent contacts such as friends, family members, frequently visited social groups or merchants, etc.

One advantage of the present system is that it can obtain information in the categories above from a patient's social network. For example, the system is configured to infer a patent's state of being through the patient's social network, for example on Twitter or Facebook. A patient's social behavior on Twitter or Facebook can be monitored and abnormal or normal behaviors are identified to infer the state of being. Such inference may be based on statistics of patient's activities, contents of patient's tweets or postings, or comments from members of patient's extended social circles. For example, if a patient regularly tweets on Twitter, a sudden reduction of number of daily tweets may suggest a change of mood of the patient. As another example, the patient regularly "checks in" to a local coffee shop using a social network's "check in" function or an application therefor, if the patient does not check in the coffee shop for a few weeks, which the patient regularly does, it may indicate that the patient is experiencing unusual pressure or additional workload. If a patient makes a post showing that he or she enjoys a lot of greasy food during a party, or "checks in" to a fast food location known for greasy, fatty food, the system could add that data to the recent activities 208b. If many members of the patient's network (e.g., the social circles of the patient for "work" or "family") experience some type of flu-like symptom, the system could add that information into the state of being data of the patient as a medical trend, and can thereby make a correlation between the patient's health status data (i.e., reporting flu-like symptoms) and the trend. Similarly, if the patient database shows other patients reporting flu in the patient's geographical area, the inference engine 110 can infer based on the patient's health status data of flu-like symptoms that there is a likelihood of flu. The system may also obtain information from other medical resources such as WebMD.com to have the most updated protocol to treat a particular symptom experienced by the patient.

Figure 3:
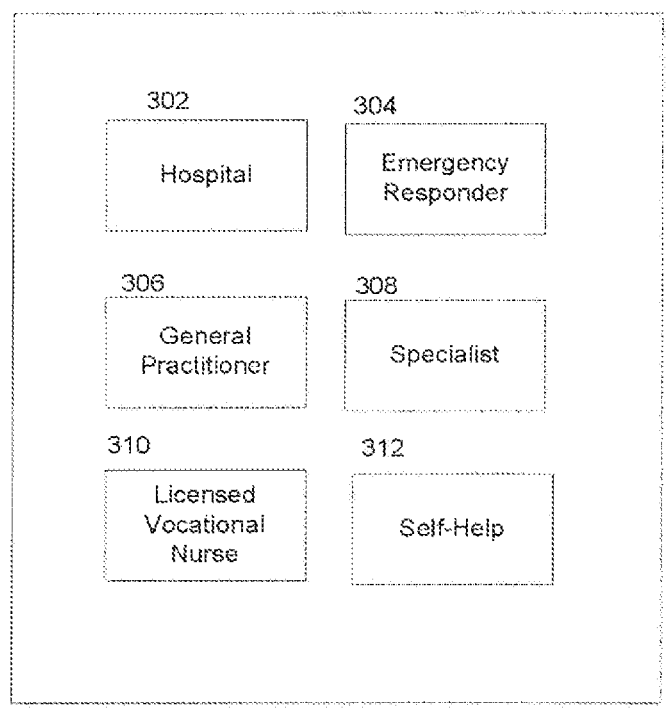
FIG. 3 illustrates exemplary health care providers according to an embodiment of the present disclosure.

FIG. 3 illustrates non-limiting exemplary health care providers according to an embodiment of the present disclosure. The health care providers 106 comprise hospitals 302, emergency responders 304, general practitioners 306, specialists 308, licensed vocational (or practical) nurses (RN, LPN, Advanced Practice Nurse) 310, and self-help (including entities that assist in providing self-help) 312. When a patient is in need of some treatment, a patient is freely able to choose any of the healthcare providers for help. As noted above, when a patient is making a decision without any professional assistance, the patient may choose a level of care that exceeds or fails to meet the actual medical need. In the case of choosing unnecessary care, this can abuse the healthcare system and delay other patients who may need more timely treatment. For example, many patients seeking emergency care may only need a scheduled visit to a general practitioner or a nurse, physician assistant or even only self-treatment. Embodiments described herein enable a patient to choose the right level of health care so that the patient is treated timely and effectively without wasting resources of the health care system. Similarly, as described herein, embodiments as described herein also enable a patient to identify and obtain urgent care more efficiently when that is needed.

The information of these health care providers 106 is stored in the patient database 114. The system, upon a call from the patient, selects the proper health care provider for the patient and routes the patient's call to the health care provider. When a patient is incapacitated, the present system can summon emergency care and provide the caregivers with the medical information of the patient. In this way, the potential for misdiagnosis or delayed diagnosis due to lack of information is reduced.

Figure 4:
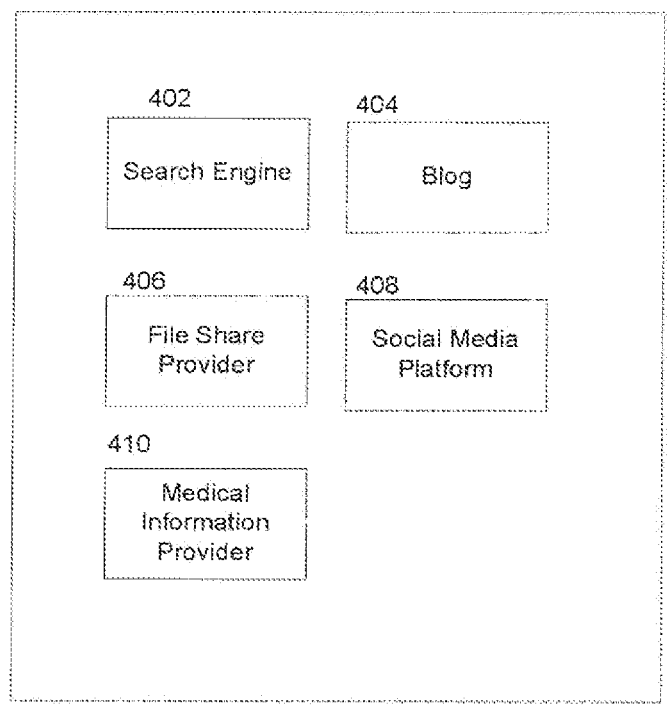
FIG. 4 illustrates exemplary social networks that the present system can obtain information about the patient according to an embodiment of the present disclosure.

FIG. 4 illustrates exemplary internet-based patient information sources 108 including information networks and social networks that the present system can obtain information about the patient according to an embodiment of the present disclosure. The internet-based patient information sources 108 may comprise search engines 402, blogs 404, content share servers 406, social media 408, and medical information providers 410. The search engines 402 may comprise Google, Yahoo, Bing, Baidu, etc. The search engines 402 may store logs about search strings, search results associated with each search, viewed results among the searched results, view time of a particular content, identification associated with each search such as geographical locations, IP address, or email address. The blog 404 may comprise Blogger, WordPress, LiveJournal, Blog, etc. The content sharing server 406 may be operated by a provider that provides file storage and sharing services, such as BitTorrent, EMule, FileSonic, DocShare, etc. The content sharing server 406 also keeps a log of file sharing history and may, upon an agreement, provide the log of file sharing history to another party. The social media 408 may comprise Twitter, Facebook, MySpace, Google+, LinkedIn, Foursquare, YouTube, etc. An account is typically required to use these social services. Activities of a patient on these social media can be tracked, for example, by using the patient's account name or a patient ID. In another embodiment, patients may agree to have information tracked, either by granting permission to an application on or interfacing with the social network, or by subscribing or "friending" an entity associated with the inference engine 110 that then has access to track the patient. The medical information providers 410 may comprise WebMD, HealthCentral, Local Health, CNN Health, MayoClinic, NIH etc. The present system uses these providers to obtain new protocols to treat a symptom or to obtain a medical trend associated with a symptom or a class of patients.

Figure 5:
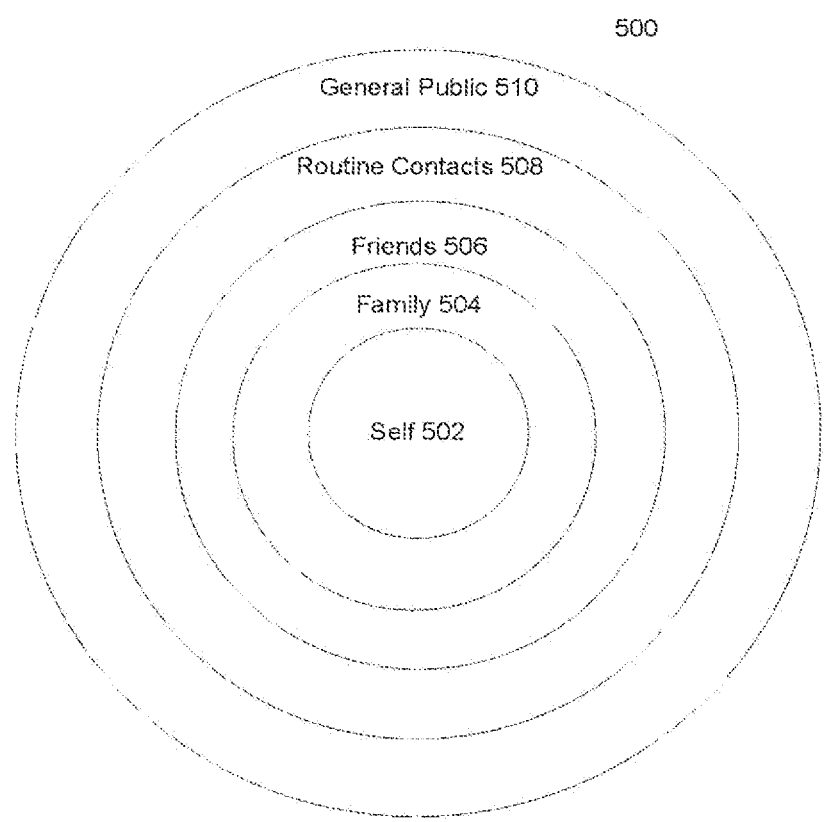
FIG. 5 illustrates an extended social circle on the social networks used by the patient according to an embodiment of the present disclosure.

FIG. 5 illustrates an example of an extended social circle 500 on a social media used by the patient according to an embodiment of the present disclosure. The extended social circle 500 comprises self 502, family 504, friends 506, routine contacts 508, and general public 510. The self circle 502 may comprise the patient himself or herself. On the social networks, information on the self circle 502 comprise search strings input by the patient, viewed and searched results by the patient, comments posted by the patient, interested topics of the patient, friends of the patient, routine activities of the patient, etc. Information from self circle 502 also comprises statistics about the patient associated with use of the social networks, including for example time spent on each social network, frequency of visit to each social network, number of post or tweets or searches conducted on each social network, specific time of the day that the patient uses the social network, etc. The family circle 504 may comprise patient's spouse, children, parents, cousins, and other relatives. Their comments on the patient's social activities, feelings, and moods are used to infer the state of being of the patient. The friend circle 506 may comprise patient's classmates, workmates, and any person marked as a friend by the patient. The routine contact circle 508 may comprise patient's neighbors, local retailers, local food store owners, local bagel and coffee shop owners, mailman, etc. Comments from family members, friends, and routine contacts on the patient's social activities, feelings, and moods can be used to collect data on and infer the state of being of the patient as described herein. Comments or frequency of "check-in" data also can be used to help remove any inaccuracy of information obtained from the patient's own description. The general public circle 510 may comprise information made available to the entire social network. As will be appreciated, although a patient's network is shown as concentric circles, a patient's networks can take any configuration and overlap in any number of ways, and indeed, a social network may allow a user to self-define his or her network, as is the case with Google+. Also, the patient's network data can be correlated with data from other patients in the network or their respective networks, for example, with correlations by geography using a geographical information system (GIS), as is well-known in the art.

By using an extended social network to infer patient's state of being, not only additional information about the patient is obtained, but also reliability and accuracy of information could be enhanced. On the social networks, people or entities in each circle may post information about the patient in different aspects. Family members or friends may post information that reveals recent activities of the patient who may fail to reveal that information to a medical practitioner or who may be incapacitated. Neighbors or coffee shop owners may talk about a patient when a patient changes his or her daily schedule or errands. The general public or geographical networks may show the extent of the spread of any seasonal diseases or may show some common activities that may be important to diagnosis of a patient's health. Additionally, the present system is capable of correlating medical conditions of multiple patients, including but not limited to symptoms, age, social activity, mood, prescription, and geographical location.

Figure 6:
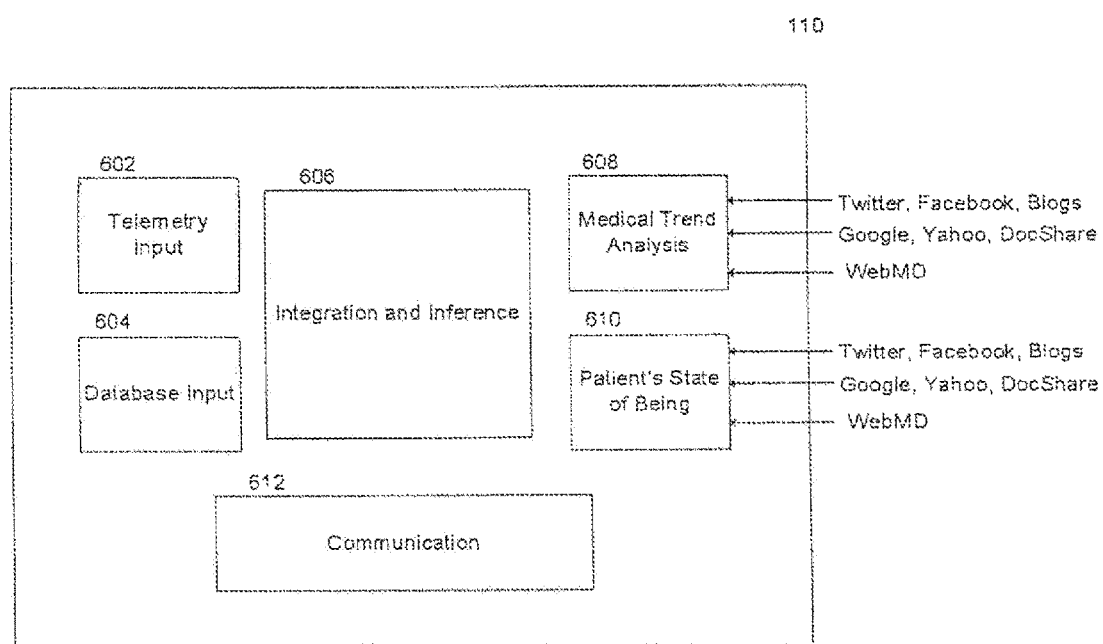
FIG. 6 illustrates exemplary functional modules of the inference engine 110 according to an embodiment of the present disclosure.

FIG. 6 illustrates exemplary functional modules of the inference engine 110 according to an embodiment of the present disclosure. The inference engine 110 may be a computer system or server, which comprises a telemetry input module 602, a database input module 604, an integration and inference module 606, a medical trend analysis module 608, a patient's state of being module 610, and a communication module 612. The telemetry input 602 receives telemetry data from the monitoring component 104 and transmits the telemetry data to the integration and inference module 606. The database input 604 receives input from the symptom database engine 112 and the patient database 114 and transmits the input to the integration and inference module 606. The medical trend analysis module 608 takes data from at least one social network and determines a medical trend associated with the patient's symptom or symptoms. The patient's state of being module 610 also obtains data from social networks and determines the state of being of the patient and other medical status information of the patient. An example of an analysis performed using a medical trend analysis module 606 and the patient's state of being module 610 may be those similar as disclosed in U.S. Application 60/505,402, "SYSTEM AND METHOD FOR PERFORMING PHARMACOVIGILANCE," the entirety of which is incorporated herein by reference. In one embodiment each individual social network has a dedicated application in the medical trend analysis module 606 and the patient's state of being module 610 to analyze data from that social network due to content and format of those data. The integration and inference module 606 integrates data from different sources and applies those data against the symptom database engine to determine the proper level of health care for the patient. The functions of the integration and inference module 606 will be described in more detail in the following part of the present disclosure. The communication module 612 communicates with the patient and/or the proper health care provider to convey the results of the integration and inference module 606.

As described herein, the inference engine 110 is capable of taking quantitative, real-time and time series in situ measurements, monitoring data from social networks for patient's state of being, monitoring data from social networks from perspective of caregivers for patient's state of being, and monitoring data from social networks for trends in treatment outcomes in population. The inference engine 110 with all the input is capable of providing real-time delivery of information related to current quantitative measurements, patient state of being, and population indicators. The inference engine 110 may also refer to currently available medical expert systems and clinical decision support systems, such as Zynx Health, ESAGIL, PEMSoft, MYCIN, HealthFlow, SimulConsult, and Diagnoz-it, when determining a treatment for a person.

FIG. 7 illustrates a record 700 of the symptom database engine 112 according to an embodiment of the present disclosure. The symptom database engine 112 stores a plurality of records 700, each associating a symptom with possible causes and suggested treatments. For example, if a symptom 702 comprises fever, the possible cause 704 may comprise a plurality of situations that may cause a fever, and the suggested treatment 706 lists a plurality of possible treatments corresponding to the possible situations. It is noted that FIG. 7 is merely illustrative of a logical record.

Many representations to store, retrieve, search for, or modify all or parts of the illustrated stored content are well known in the state of the art.

The symptom database engine 112 also includes functions to determine a possible cause or causes of a symptom. Such functions may be in forms of an expert system or a decision tree. Examples of web-based expert system includes those software owned and managed by EasyDiagnosis, a division of MatheMEDics such as www.easydiagnosis.com and those described in the article, "Internet-Based Expert System," Ralph Grove, Expert Systems, July 2000, Vol. 17, No. 3, pp. 129-135, the entirety of which are incorporated herein by reference. The integration and inference engine 110 transmits the symptom of the patient and the medical status of the patient to the symptom database engine, which determines the possible causes and possible treatments.

As an example, the symptom database includes a functional module associated with congestive heart failure (CHF), which represents a condition in which the heart cannot pump enough blood to meet the needs of the body. Heart failure occurs after the heart muscle has been damaged or weakened by another primary cause, such as high blood pressure, coronary artery disease, or certain kinds of infections. Depending on the cause, heart failure can occur gradually, over many years, while the heart tries to compensate for its loss of function, or it may occur more quickly if too much of the heart muscle is damaged at once. A common cause of heart failure is coronary artery disease (CAD), a narrowing of the small blood vessels that supply blood and oxygen to the heart. Symptoms associated with CHF may include shortness of breath, especially with activity, or when lying down, swelling of feet and ankles, fatigue and weakness, persistent cough or wheezing cough that may be accompanied by white or blood-tinged phlegm, rapid weight gain, irregular or rapid heartbeat, change in urine production (increase or decrease, need to urinate at night), nausea, loss of appetite, decreased alertness, needing more than two pillows to sleep, and increase of respiration rate.

Heart failure may suddenly get worse due to angina, eating high-salt foods, heart attack, infections or other illnesses, and not taking medicines correctly. Each of the above symptoms may be evaluated based on a well-known scale. For example, the fatigue and short of breath may be characterized to show the severity on a New York Heart Association scale of 0-10 (10 being very severe fatigue or shortness of breath). Heart failure may also be functionally classified based on the New York Heart Association functional classification. The classes (I-IV) are: Class I: no limitation is experienced in any activities; there are no symptoms from ordinary activities; Class II: slight, mild limitation of activity; the patient is comfortable at rest or with mild exertion; Class III: marked limitation of any activity; the patient is comfortable only at rest; and Class IV: any physical activity brings on discomfort and symptoms occur at rest. Medical treatments to congestive heart failure may include medication, lifestyle changes, and even transplantation.

As an illustrative example, a patient experiencing fatigue and shortness of breath may interact with the system to determine the need for treatment. The symptom database engine 112 receives input about a patient who has symptoms potentially related to heart failure from the integration and inference engine 110. The input may include information about state of being of the patient, medical history of the patient, telemetry of the patient, and patient's self description of the symptoms. The symptom database engine 112 may access the medical history of the patient who has a history of congestive heart failure and is currently on several medications, for example Hydrochlorothiazide, a diuretic. The symptom database engine 112 may find through the self-description of the patient that the patient, during the past three days, feels fatigue very easily, wakes up a few times during sleep, uses three pillows during sleep, and experiences shortness of breath. The symptom database engine 112, through the state of being analysis, may find that the patient has family members close to his or her residence and has social events with them regularly. For example, the symptom database engine 112 may also find that three days ago (Day 1) the patient attended a party with those family members and consumed an unusual and excessive amount of salty food. The symptom database engine 112 may also find that on (Day 2) the patient complained about fatigue on Facebook and difficulty sleeping and substantially reduced the number of tweets he or she usually does. The symptom database engine 112 may also find through telemetry data records about patient's heart rate, respiration rate, weight gain, sleeping number and inclination of patient's sleep number bed, and temperature of patient's residence. For example, the patient may be instructed to daily weigh him or herself on a telemetry enabled scale that records the weights longitudinally. Telemetry data from the smart scale shows a 5-6 pound weight gain on Day 3. GPS tracking combined with respiratory data may also show that at a specific time on Day 3 the patient was walking a number of flights of stairs, and had to take a rest midway.

The comprehensiveness of the information about the patient allows the symptom database engine 112 to evaluate the medical situation of the patient and make proper recommendations. For example, where a patient is experiencing fatigue and shortness of breath, the symptom database engine based on the medical history data, state of being data, and telemetry data, may determine that the patient's weight fluxes, resting and active heart rates, and probable dietary changes have a high probability of being due to orthopnea, which without adjustments could lead to pulmonary edema. The symptom database engine 112 can be configured to assign a classification score which indicates that while the patient should seek medical attention and see a doctor by appointment as soon as possible, the patient does not need immediate emergency care and intervention. The symptom database engine may also provide a health care professional who is handling the patient interaction with treatment recommendations, for example, doubling the dose of a diuretic the patent is prescribed (e.g., Hydrochlorothiazide).

On the other hand, the symptom database engine 112 may determine that the data is showing an acute or imminent cardiac event, which requires an emergency visit. For example, the symptom database engine 112 may also determine that the rapid weight gain of five pounds in three days indicates a sudden deterioration of CHF and requires immediate medical intention. Alternatively, the symptom database engine 112 may need more information about the patient and communicate the needs of more information to the inference engine or initiate a direct dialog with the patient.

The operation of the symptom database engine 112 may be triggered based on a call from the patient or may be triggered based on other thresholds. For example, a sudden change of the telemetry data such as heart rate or weight gain may trigger the operation of the symptom database engine 112. Or the symptom database engine 112 may request or accept data periodically (e.g., push or pull messaging, polling, etc.).

As shown above the symptom database engine 112 may output a plurality of recommendations. Each recommendation may include a summary of the symptom, possible causes of the symptom, and actions needed to treat the situation, such as take immediate medication, visit a doctor, or require emergency care. Optionally, each recommendation may be assigned a probability showing how likely the recommendation is correct or close to the true cause or causes. This can be implemented using techniques known in the art, including without limitation, for example, an expert system or decision tree based algorithm as described above, which as it obtains more information inputs for answers, it can deductively assess with greater accuracy an appropriate level of care. As will be appreciated, data can be also grouped and weighted to prioritize care assessments, for example, to bias critical needs for immediate care.

FIG. 8 illustrates a record 800 of the patient database 114 according to an embodiment of the present disclosure. The patient database 114 stores important information of a patient 102. These information may comprise patient ID 802, a social ID used in a social network 804, a general practitioner associated with the patient 806, specialist of the patient 808, hospital preferred by the patient 810, emergency responder for the area 812, information about family members of the patient 814, information about the patient's friends 816, routine contacts of the patient 818, regular activities of the patient 820, and other information 822. The patient ID 802 comprises patient's name, address, age, gender, birth date, and contact information. The patient ID 802 may also comprise a randomly generated number to be used to identify the patient when information of the patient is transmitted or stored in the present system. Such a random number would provide additional protections to the patient's privacy even when the transmitted information is intercepted. The social ID 804 comprises patient's account names for each social network, email address, user IDs and nicknames used on social networks. Information about health care providers such as the general practitioner 806, the specialist 808, the hospital 810, and the emergency responder 812 comprises address, license number, and contact information. The information about members in the extended social circles such as family 814, friend 816, and routine contacts 818 of the patient comprises similar information as that of the patient. The regular activities 820 comprises information about a patient's daily or weekly schedules such as visiting a coffee shop, doing exercise, staying with a friend, or seeing a movie. According to an embodiment, the information of emergency responder for the area 812 may not be part of the patient record, but is included in a separate table that associates the patient ID with their current geographic location (e.g, via geofencing) to determine the emergency responder to contact. It is noted that FIG. 8 is merely illustrative of a logical record. Many representations to store, retrieve, search for, or modify all or parts of the illustrated stored content are well known in the state of the art.

Figure 9:
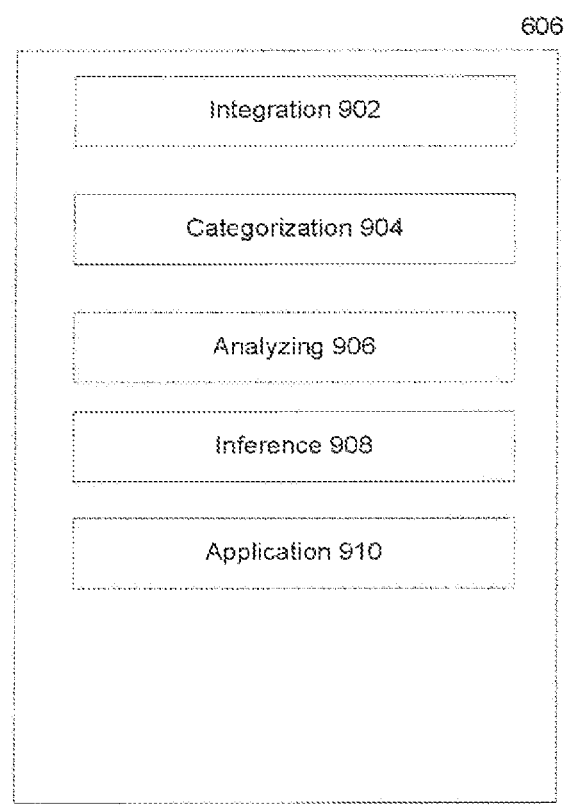
FIG. 9 illustrates functional modules of the integration and inference module 606 according to an embodiment of the present disclosure.

FIG. 9 illustrates functional modules of the integration and inference module 606 according to an embodiment of the present disclosure. The integration and inference module 606 may comprise an integration module 902, a categorization module 904, an analyzing module 906, an inference module 908, and an application module 910. As data are obtained from various sources, the integration module 902 analyzes the raw data, such as search strings, comments, tweets, blogs, and pictures, and integrates data from the various sources into a consistent format in a temporal order. The categorization module 904 classifies the integrated data to one or more categories such as state of being, recent activities, self-description, medical history, or telemetry. The analyzing module 906 analyzes data in each category to determine the priority, reliability, and consistency of each piece of data. The inference module 908 infers mood, emotion, or other data about the patient's state of being. The application module 910 then applies data against the symptom database engine 112 to determine the proper level of health care. The application module further determines whether rerouting of the patient's communication to a health care provider is needed or not.

When the system 100 is in operation, the patient's sensing devices send a stream of data to the inference engine 110. The patient's data stream also goes to the symptom database engine 112. This flow could be direct from the patient's sensing devices as well. If triggered, the symptom database engine 112 alerts a match for an abnormal outcome. Trends from the medical art, such as new protocols or interaction data with current patient protocols are analyzed by the medical trend analysis module 608, which takes input from traditional sources, such as New England Journal of Medicine as well as web-oriented sources, such as WebMd. In addition, the module takes input from social media sources as described herein. The state of being trend analysis module 610 correlates trends from the user's social networks, whether including social media or blogs or other unconsolidated sources, to determine the state of being of the patient. With the diagnostic data, the inference engine can make an enhanced diagnosis and proactively alert the patient 102, caregiver 106, or emergency responder 812.

The patient 102 can also call or send a message to the inference engine 110 to find out the best course of action for a given symptom or situation. This can, for example, be by telephone through an IVR system, a smartphone or tablet application, or over the internet. The inference engine can also connect the patient, automatically, to a Public Safety Access Point (PSAP—911), their doctor or nurse, their caregiver, or a family member. The patient database 114 comprises identifying information required by the state of being trend analysis module 610, so it knows which individuals to be monitoring. The patient database 114 also has the treatment regimen information required by the medical trend analysis module, so it knows what treatments and protocols to be monitoring. The patient database also comprises information about the patient's caregivers 106 and emergency responders 812.

Figure 10:
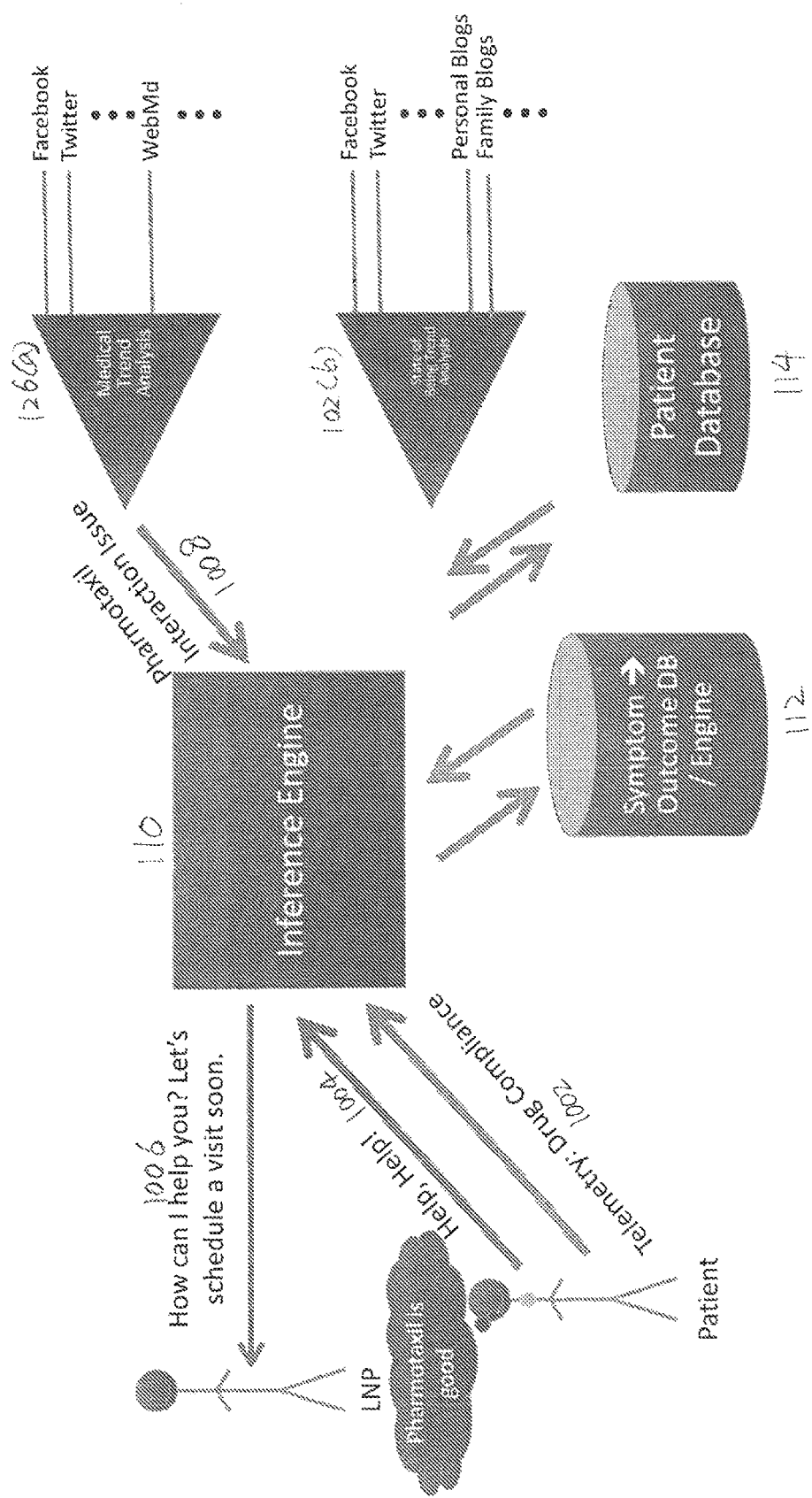
FIG. 10 illustrates an exemplary operation of the system and method according to an embodiment of the present disclosure.

FIG. 10 illustrates an exemplary operational flow of the system according to an embodiment of the present disclosure. In this scenario, a patient has concerns about his or her medical conditions. For example, a patient is taking Pharmotaxil, a made-up name for a drug. Based on the data sent by the monitoring system 104, the system notes the patient's compliance with drug regimen (1002). Medical trend analysis 126(a) identifies that Pharmotaxil has elevated risk for imminent heart attack if the patient has a slight fever and elevated pulse rate and notifies the inference engine 110 (1008). Telemetry data indicates the patient has normal temperature and heart rate (1002). When a patient sees issues raised in the popular press, the patient contacts with the present system about the issue (1004), for example using a panic button on a monitoring device that comprises a communication device which sends a message to the inference engine 110. The present system, having data indicating Pharmotaxil presents a risk of heart attack, sends a message to the primary care physician or calls the primary physician and transmits the inquiry to the physician's office (1006). A nurse can now handle the call because he or she already knows why the patient is calling and can schedule an office visit to reconsider a treatment protocol in a timely but not emergency basis, and can assure the patient that they are being monitored if an emergency situation arises. Non-limiting examples of calls referred to in the present disclosure comprise conventional calls placed over the public switched telephone network; real-time interactive voice, video, or instant messages (such as Skype, Vonage, Google-Talk, AOL Instant Messenger, etc.); or asynchronous voice, video, or text messages (such as email, wall postings, short message service (text messages), etc.

Figure 11:
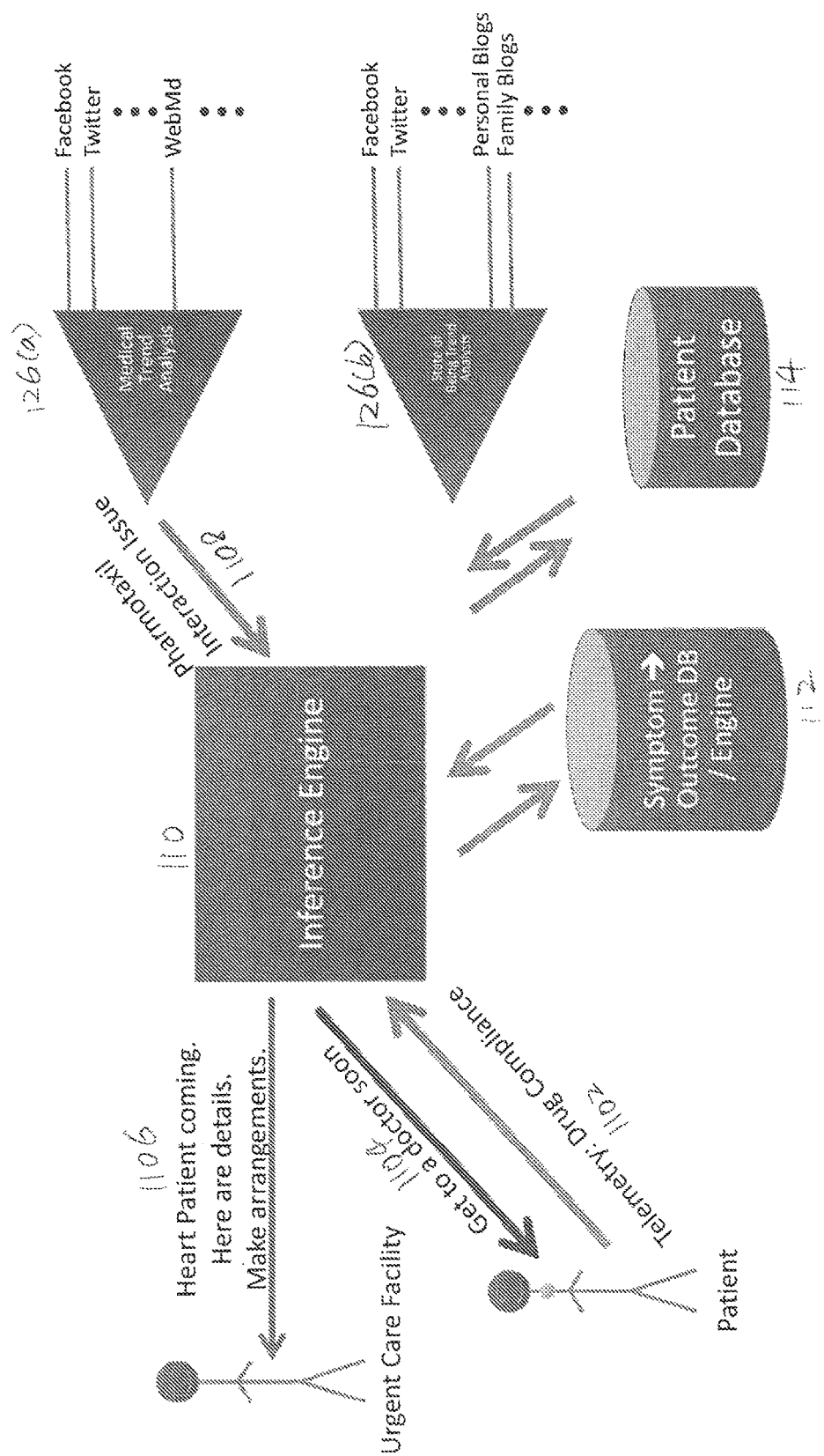
FIG. 11 illustrates another operation of the system and method according to an embodiment of the present disclosure.

FIG. 11 illustrates another operational flow of the system according to an embodiment of the present disclosure. In this scenario, a patient is at risk. Again, a patient is taking Pharmotaxil. Medical trend analysis 126(a) notes Pharmotaxil has elevated risk for imminent heart attack if the patient has a slight fever and elevated pulse rate (1108). Telemetry data from the patient indicates the patient has a fever of 101° F. and a pulse rate of 115 (1102). The inference engine 110 then proactively alerts caregivers and, if appropriate, emergency services (1106) and the patient (1104) to get patient to an urgent care facility before a heart attack occurs.

Figure 12:
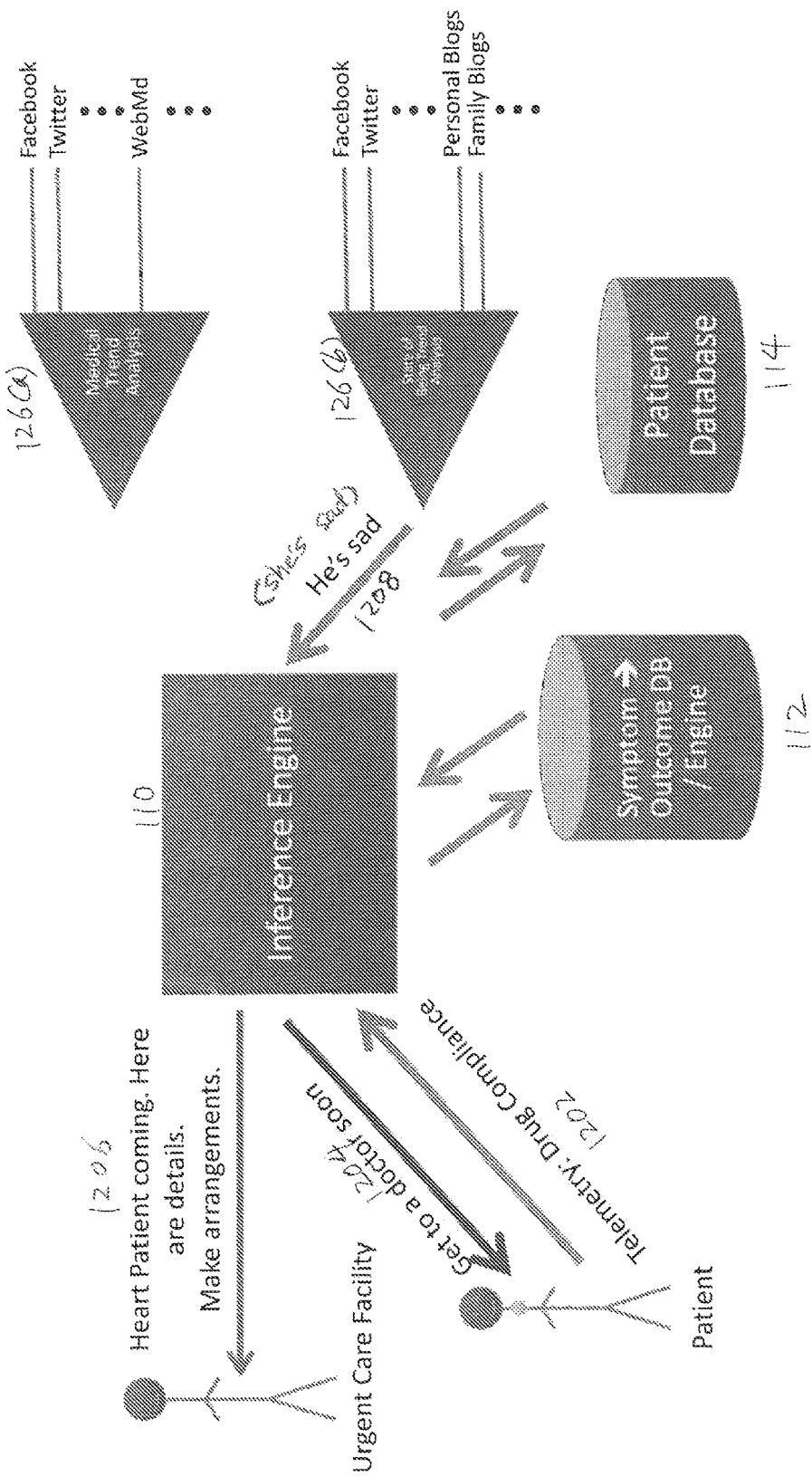
FIG. 12 illustrates another operation of the system and method according to an embodiment of the present disclosure.

FIG. 12 illustrates another operational flow of the system according to an embodiment of the present disclosure. In this scenario, the state of being of a patient plays an important role in making a medical decision. Again, a patient is taking Pharmotaxil. A state of being trend analysis module 126(b) analyses data via social networks and determines the patient is depressed, for example, by an uptick in attending unhealthy fast food locations and posts from himself or herself and his or her family using language indicating depression. The state of being trend analysis module 126(b) notifies the inference engine about the depression of the patient (1208). The system polls telemetry data to determine patient status (1202). The symptom database 112 determines that there is an elevated risk for suicide if the patient is slightly depressed. The system proactively notifies caregivers to attend to the patient and to monitor him or her (1206). Emergency care is not explicit in this situation; however the system may be configured to send a message to the appropriate health care provider, such as for example a treating psychologist or psychiatrist. The system also notifies the patient about his or her medical situation (1204).

Figure 13:
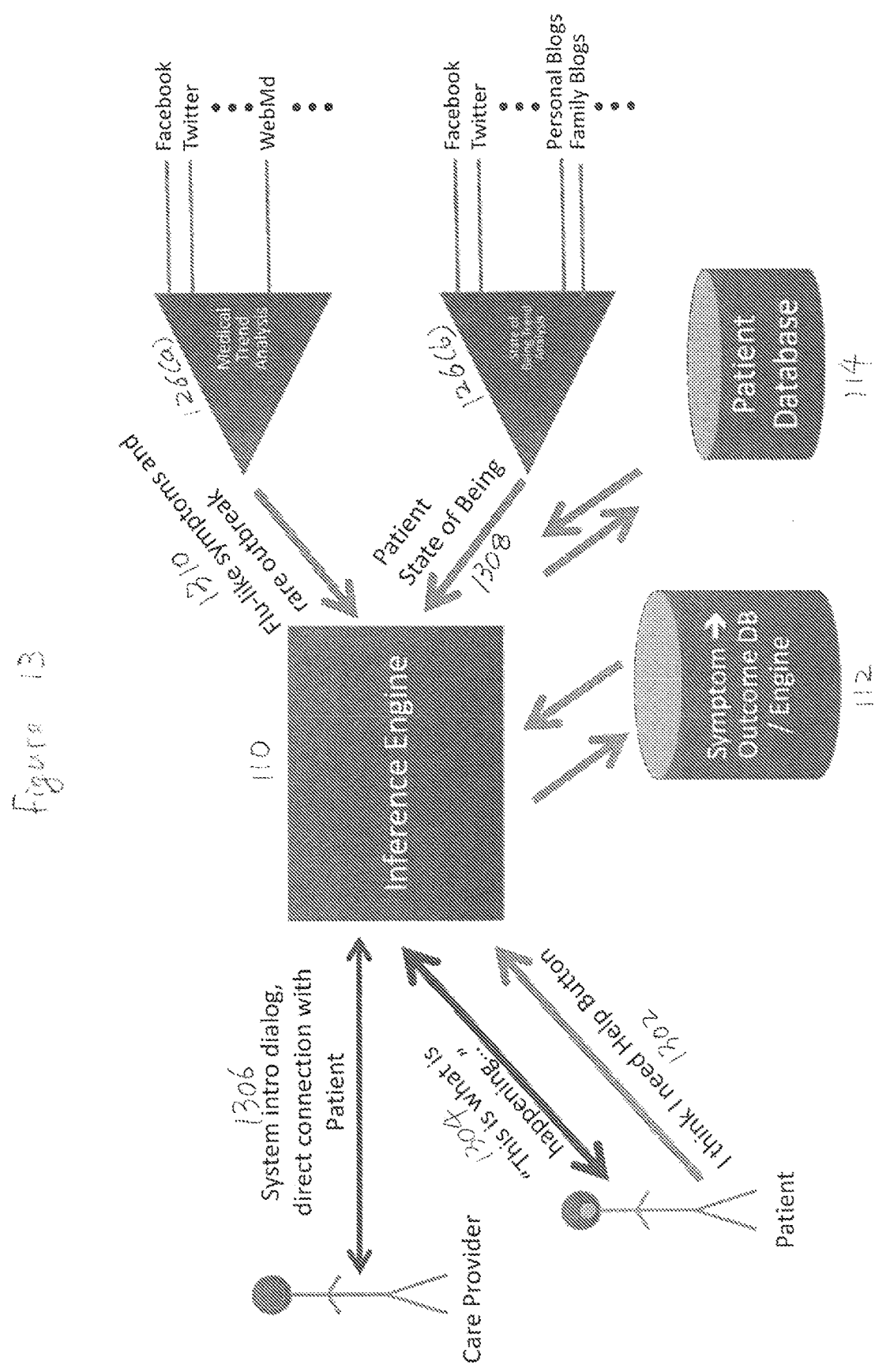
FIG. 13 illustrates another operation of the system and method according to an embodiment of the present disclosure.

FIG. 13 illustrates another operational flow of the system according to an embodiment of the present disclosure. In this scenario, the system routes the call from a patient to a proper health care provider. A patient has flu-like symptoms and presses a "call health professional" button on the communications device (1302). The inference engine 110 analyses the state of being data, medical telemetry data, patient history, and patient regimen and determines the patient has either a cold, the flu, or is suffering from a rare outbreak of a disease (1310 and 1308). The system connects the patient to a care provider, in this instance a nurse and not a physician, as the inference engine cannot determine if cold, flu, or an outbreak of a rare disease is the proper diagnosis (1306). The system informs the nurse, via voice messaging, multimedia, or integrated EHR messaging, information comprising patient history as well as up-to-date information about the disease outbreak epidemiology. The system also notifies the patient (1304). A nurse or physician assistant performs additional diagnostic interview to differentiate between cold and flu, or the rare illness. The system notes the interaction with the patient for the professional caregiver's (e.g., the doctor's) files. The note comprises information showing that the call was directed to an appropriate caregiver to triage importance.

Figure 14:
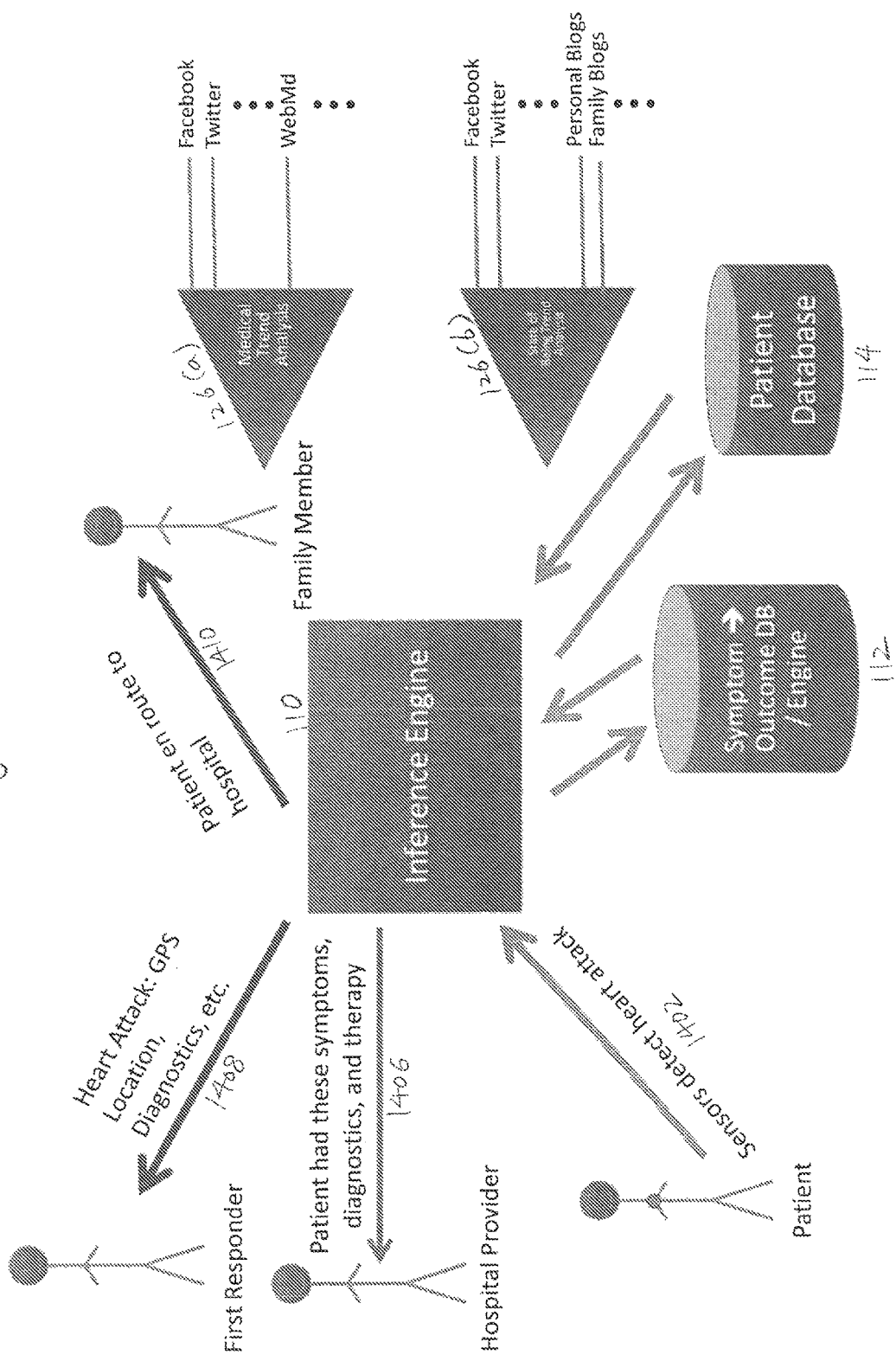
FIG. 14 illustrates another operation of the system and method according to an embodiment of the present disclosure.

FIG. 14 illustrates another operational flow of the system according to an embodiment of the present disclosure. In this situation, patient's heart stops and the system notifies all the related parties who are proper to receive patient's medical situation. The system knows the situation based on telemetry data (1402). The system calls 911 and informs the emergency responder about the location of the patient and the situation of the patient—heart attack occurred (1408) and notifies the hospital that will accept the patient (1406). The system can be configured to be fully capable to interoperate with NG-911, using rich media to alert emergency services with relevant information, including accurate location information. The system can make the appropriate medical history information available in a timely basis to urgent care facilities practitioners. The system also calls patient's cardiologist based on the telemetry data (not shown in FIG. 14). The system also calls patient's family members (1410).

Figure 15:
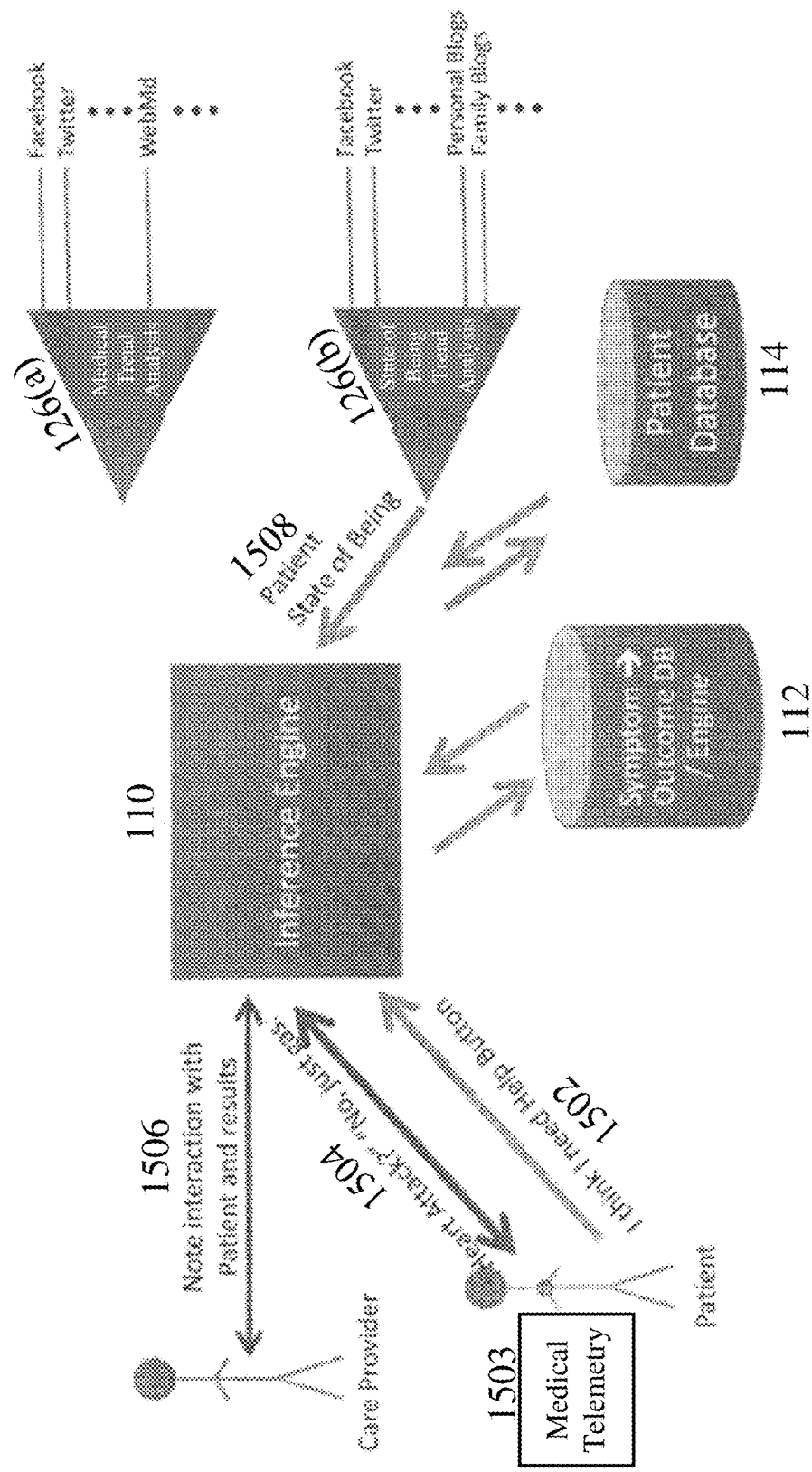
FIG. 15 illustrates another operation of the system and method according to an embodiment of the present disclosure.

FIG. 15 illustrates another operational flow of the system according to an embodiment of the present disclosure. As shown, a patient has chest pains while exercising; the patient is concerned that he or she may have a heart attack. The system infers and is aware the patient is exercising by its analysis of medical telemetry (e.g., from a smart watch that measures heartbeat and other telemetry) (1503) and state of being data (1508). The patient depresses a help button (e.g., on a smart phone app or the smart watch) sends a message asking the system if a heart attack is occurring (1502). The system, based on information obtained from social networks and telemetry data, tells the patient that the patient likely has some gas in his or her stomach rather than having a heart attack (1504). The system also recommends some OTC treatment such as Turns to the patient. Alternatively, the system notes diagnosis in EHR for the patient and allows professional to review the situation and consider the 1:1,000,000 chance of something missed or so rare it is not in the literature or is trending (1506).

The phrase "an embodiment" as used herein does not necessarily refer to the same embodiment, though it may. In addition, the meaning of "a," "an," and "the" comprise plural references; thus, for example, "an embodiment" is not limited to a single embodiment but refers to one or more embodiments. As used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise.

While this invention has been described in conjunction with the specific embodiments outlined above, it is evident that many alternatives, modifications, and variations will be apparent to those ordinarily skilled in the art. Accordingly, the preferred embodiments of the invention as set forth above are intended to be illustrative, not limiting. Various changes may be made without departing from the spirit and scope of the inventions as defined in the following claims.

What is claimed is:

1. A system for assisting a patient to select a proper form of treatment, comprising:
    an interface for a monitoring section that monitors a symptomatic event of the patient;
    an electronic processor including an inference section that infers the patient's psychiatric or psychological mental state of being based on social behavior information about the patient from at least one social network, wherein the social behavior information is limited to the patient's activity on the at least one social network which the patient has provided consent to monitor;
    a storage device including a patient database that stores the patient's information; and a symptom engine that stores symptom data of psychologic or psychiatric conditions;

wherein the inference section processes the patient's psychiatric or psychological mental state of being to compile mental state data, and the symptom engine compares the mental state data against symptom data stored in the symptom engine to determine a treatment response;

wherein the inference section further infers a trend based on a symptom of the patient and the social behavior information obtained through the at least one social network;

wherein the system recommends a treatment based on an assigned probability indicating a likelihood of the treatment recommendation being correct; and wherein the system transmits information regarding a change in the patient's symptomatic event to the inference section only if the system determines the change to be significant based on an internal threshold, thus reducing the amount of traffic through the network.

2. The system according to claim 1, wherein the social behavior information comprises information relating to a select social circle or a social media self-circle defined by the patient.

3. The system according to claim 1, wherein the social behavior information from the at least one social network is limited to data from a family social circle.

4. The system according to claim 1, wherein the inference section correlates symptoms and state of being from multiple patients.

5. The system according to claim 1, wherein the monitoring section comprises a mobile wireless monitoring device.

6. The system according to claim 1, where in the system comprises:
an interface with an aggregation component configured to aggregate information from the monitoring section about the symptomatic event of the patient.

7. The system according to claim 1, wherein the system contacts a health care provider when a medical treatment is needed.

8. The system of claim 1, wherein the social behavior information further comprises comments from others regarding the patient on the at least one social network.

9. A method for assisting a patient to select a proper form of treatment, comprising:
remotely monitoring a symptomatic event of the patient by a sensor;
inferring the patient's psychiatric or psychological mental state of being based on social behavior information of the patient obtained from an at least one social network, wherein the social behavior information is limited to the patient's activity on the at least one social network which the patient has provided consent to monitor;
electronically storing the patient's information; and
electronically storing symptoms of psychologic or psychiatric conditions;
wherein the inferring step applies the symptomatic event and the psychiatric or psychological mental state of being to compile mental state data to be compared against the stored symptoms to determine a treatment response;
wherein inferring further comprises inferring a medical trend based on a symptom of the patient, information obtained through the at least one social network, and information obtained by correlating symptoms and states of multiple patients; and
wherein the method recommends a treatment for the symptomatic event to a health care provider based on an assigned probability indicating a likelihood of the treatment recommendation being correct, thus improving the accuracy of the treatment recommendation.

10. The method according to claim 9, wherein storing the patient's information includes storing medical history information of the patient from one or more health care providers, and the inferring further comprises inferring a psychiatric or psychological mental state of being of the patient based on the stored medical history information of the patient and social behavior information obtained from the at least one social network.

11. The method according to claim 9, where in the inferring comprises correlating symptoms and state of being from multiple patients.

12. The method according to claim 9, wherein the monitoring comprises using a mobile wireless monitoring device.

13. The method according to claim 9, wherein the method comprises:
receiving aggregated information about the health status of the patient from an aggregation component that aggregates the symptomatic event information from the patient.

14. The method according to claim 9, wherein the method comprises contacting a health care provider when a medical treatment is needed.

15. The method of claim 9, wherein the social behavior information further comprises comments from others regarding the patient on the at least one social network, wherein the social behavior information comprises information relating to a select social circle or a social media self-circle defined by the patient.

16. A non-transitory storage medium storing a program that, when executed, causes a processor to execute a method for assisting a patient to select a proper form of treatment, the method comprising:
remotely monitoring a symptomatic event data of the patient;
filtering out insignificant information from the monitored symptomatic event data;
inferring the patient's psychiatric or psychological mental state of being based on social behavior information of the patient obtained from at least one social network which the patient has provided consent to monitor;
electronically storing the patient's information including the symptomatic event data; and
electronically storing symptoms of psychologic or psychiatric conditions;
wherein inferring comprises comparing the symptomatic event data and psychiatric or psychological mental state of being data against the stored symptoms to determine a treatment response, calculating a plurality of treatment responses based on probabilities that the treatment responses are correct, and transmitting the plurality of treatment responses to a health care practitioner, thus providing the health care practitioner a plurality of diagnoses that may not have been initially apparent.

17. The storage medium according to claim 16, wherein inferring further comprises inferring a medical trend based on a symptom of the patient and information obtained through social network.

18. The storage medium according to claim 16, wherein storing the patient's information includes storing medical history information of the patient from one or more health care providers, and inferring further comprises inferring a psychiatric or psychological mental state of being of the patient based on the stored medical history information of the patient and information obtained through the at least one social network.

19. The non-transitory storage medium of claim 16, wherein the social behavior information further comprises comments from others regarding the patient on the at least one social network, and wherein the social behavior information comprises information relating to a select social circle or a social media self-circle defined by the patient.

20. A system for assisting a patient to select a proper form of treatment, comprising:
- an application section hosted by the patient that monitors a symptomatic event of the patient, aggregates information about the symptomatic event of the patient and a psychiatric or psychological mental state of being about the patient based on social behavior information about the patient obtained from at least one social network, which the patient has provided consent to monitor;
- a storage section coupled to the application section that stores patient's information; and
- a symptom engine that stores symptom data of medical conditions;
- wherein the application section processes the symptomatic event and psychiatric or psychological mental state of being data and compares it against symptom data stored in the symptom engine to determine a treatment response, recommends a treatment based on an assigned probability indicating a likelihood of the treatment response being accurate, and transmitting at least one treatment response to a desired recipient.

21. The system according to claim 20, wherein the storage section is locally connected with the application section, and the application section is connected with the symptom engine via a network.

22. The system according to claim 20, wherein the application section comprises an advanced mobile phone or a tablet.

23. The system according to claim 20, wherein application section comprises a device selected from an advanced mobile phone, a tablet, or a wireless radio base station.

24. The system of claim 20, wherein the social behavior information further comprises comments from others regarding the patient on the at least one social network, and wherein the social behavior information comprises information relating to a select social circle or a social media self-circle defined by the patient.

* * * * *